US012339286B2

(12) United States Patent
Ackerson et al.

(10) Patent No.: US 12,339,286 B2
(45) Date of Patent: Jun. 24, 2025

(54) METAL-REDUCING ENZYMATIC TAG FOR OPTICAL AND ELECTRON MICROSCOPY

(71) Applicant: Colorado State University Research Foundation, Fort Collins, CO (US)

(72) Inventors: Christopher J. Ackerson, Fort Collins, CO (US); Zachary Butz, Fort Collins, CO (US); Richard Nemeth, Fort Collins, CO (US); Ryan Riskowski, Fort Collins, CO (US); Kanda Borgognoni, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 1145 days.

(21) Appl. No.: 17/266,734

(22) PCT Filed: Aug. 9, 2019

(86) PCT No.: PCT/US2019/046027
§ 371 (c)(1),
(2) Date: Feb. 8, 2021

(87) PCT Pub. No.: WO2020/036831
PCT Pub. Date: Feb. 20, 2020

(65) Prior Publication Data
US 2021/0311066 A1    Oct. 7, 2021

Related U.S. Application Data

(60) Provisional application No. 62/717,325, filed on Aug. 10, 2018.

(51) Int. Cl.
| | | |
|---|---|---|
| *C12N 9/02* | (2006.01) | |
| *B82Y 40/00* | (2011.01) | |
| *C12N 15/53* | (2006.01) | |
| *C12N 15/62* | (2006.01) | |
| *C12Q 1/26* | (2006.01) | |
| *G01N 33/58* | (2006.01) | |
| *G01N 33/68* | (2006.01) | |
| *B82Y 5/00* | (2011.01) | |
| *B82Y 35/00* | (2011.01) | |

(52) U.S. Cl.
CPC ............. *G01N 33/581* (2013.01); *C12Q 1/26* (2013.01); *G01N 33/68* (2013.01); *B82Y 5/00* (2013.01); *B82Y 35/00* (2013.01); *B82Y 40/00* (2013.01); *G01N 2333/90212* (2013.01)

(58) Field of Classification Search
None
See application file for complete search history.

(56) References Cited

U.S. PATENT DOCUMENTS

| | | |
|---|---|---|
| 6,914,265 B2 | 7/2005 | Bawendi et al. |
| 7,235,361 B2 | 6/2007 | Bawendi et al. |
| 2003/0059955 A1 | 3/2003 | Bamdad |
| 2014/0322744 A1 | 10/2014 | Zambrano et al. |
| 2021/0085807 A1* | 3/2021 | Teramura ............... A61L 31/18 |

FOREIGN PATENT DOCUMENTS

| | | |
|---|---|---|
| WO | 2006084276 A2 | 8/2006 |
| WO | 2012080551 A1 | 6/2012 |
| WO | 2013087963 A1 | 6/2013 |
| WO | 2020036831 A2 | 2/2020 |

OTHER PUBLICATIONS

Zhang, Song, et al. "Development of an electrochemical aptamer-based sensor with a sensitive Fe3O4 nanopaticle-redox tag for reagentless protein detection." Electrochemistry Communications 13.9 (2011): 928-931. (Year: 2011).*
Ni et al., "Progress toward clonable inorganic nanoparticles," Nanoscale 7:1732017327, 2015 (Year: 2015).*
Sambrook et al., Molecular Cloning A Laboratory Manual, 2nd Ed., Cold Spring Harbor, N.Y. 1989, pp. 2.43-2.84 (Year: 1989).*
Nemeth et al., "The metalloid reductase of Pseudomonas Moravenis stanleyae conveys nanoparticle mediated metalloid tolerance," ChemRxiv doi: 10.26434/chemrxiv.6267383.v1, May 2018, 25 pages (Year: 2018).*

(Continued)

*Primary Examiner* — David Steadman
(74) *Attorney, Agent, or Firm* — Haukaas Fortius PLLC; Michael Haukaas

(57) ABSTRACT

Enzymes that reduce specific metal or metalloid ions to insoluble form are important to science. Peptides isolated from yeast- and phage-display libraries can affect the size and morphology of inorganic materials during their synthesis. Herein, an Se binding peptide was fused to an enzyme capable of reducing selenite ($SeO_3^{2-}$) to a $Se^0$ nanoparticle (SeNP). The fusion of the Se binding peptide to the metalloid reductase provided size control of the resulting SeNP. The SeNP product also remains associated to the enzyme fusion. The Se binding peptide fusion to the enzyme increases the enzyme's $SeO_3^{2-}$ reductase activity. Modification of enzyme activity was absent, and the size control of particles was diminished when the Se binding peptide was added exogenously to the reaction mixture. Binding of the peptide is attributed to His based ligation that results in a conformational change to the peptide.

21 Claims, 13 Drawing Sheets
Specification includes a Sequence Listing.

(56) References Cited

OTHER PUBLICATIONS

Nemeth et al., "Biogenic nanoparticles and their application in biological electron microscopy," Dissertation, Colorado State University, 2018 (Year: 2018).*

Ansary et al., "Biomimetic Synthesis of CdSe Nanoparticles with Potential Bioimaging Applications," IJPSR, 8(6):2526-2532, Jun. 2017.

Dong et al., "One-Pot Synthesis of CdSe Quantum Dots in Aqueous Solution for Biological Labeling," J Chin Chem Soc., 60:1328-1332, Nov. 2013.

International Search Report and Written Opinion of the ISA/US in PCT/US2019/046027, dated Apr. 21, 2020; 14pgs.

Li et al., "Mechanism-Oriented Controllability of Intracellular Quantum Dots Formation: The Role of Glutathione Metabolic Pathway," ACS Nano, 7(3):2240-2248, Feb. 2013.

Li et al., "Roles of Glutathione and L-Cysteine in the Biomimetic Green Synthesis of CdSe Quantum Dots," Front. Environ. Sci. Eng., 11(6)7:1-9, Apr. 2017.

Nemeth et al., "Metalloid Reductase of Pseudomonas moravenis Stanleyae Conveys Nanoparticle Mediated Metalloid Tolerance," ACS Omega., 3(11):14902-14909, Nov. 2018.

Tian et al., "Fluorescence Dynamics of the Biosynthesized CdSe Quantum Dots in Candida utilis," Sci Rep., 7(1):2048, May 2017.

Wegner et al., "Quantum Dots: Bright and Versatile In Vitro and In Vivo Fluorescence Imaging Biosensors," Chem Soc Rev., 44(14):4792-4834, Jul. 2015.

Willner et al., "Growing Metal Nanoparticles by Enzymes," Adv. Mater., 18(9):1109-1120, Apr. 2006.

Yang et al., "Single Enzyme Direct Biomineralization of CdSe and CdSe—CdS Core-Shell Quantum Dots," ACS Appl Mater Interfaces, 9(15):13430-13439, Apr. 2017.

\* cited by examiner

A.

B.

A.

B.

METAL-REDUCING ENZYMATIC TAG FOR OPTICAL AND ELECTRON MICROSCOPY

RELATED APPLICATIONS

This application is a National Stage filing under 35 U.S.C. § 371 of International Application No. PCT/US2019/046027, filed Aug. 9, 2019, which claims priority under 35 U.S.C. § 119 (e) to U.S. Provisional Patent Application No. 62/717,325 filed Aug. 10, 2018, which applications are incorporated herein by reference.

GOVERNMENT SUPPORT

This invention was made with government support under Grant Nos. R21 EB014520 and R01 GM112225 awarded by the National Institutes of Health. The government has certain rights in the invention.

SEQUENCE LISTING

The instant application contains a Sequence Listing which has been submitted electronically in ST.25 format and is hereby incorporated by reference in its entirety. The ST.25 copy, created on Dec. 13, 2019, is named 520_024US1_SL, and is 2,786 bytes in size.

BACKGROUND OF THE INVENTION

Metal and metalloid reducing and/or oxidizing enzymes are a key component in cellular metal homeostasis. They can be involved in metal storage, for instance the ferroxidase centers in ferritin. They can also be involved in diminishing metal/metalloid toxicity, for instance by reducing species from soluble to an insoluble form, as exemplified by mercuric reductase. Nanoparticles comprised of cadmium sulfide, palladium, selenium, chromium, cobalt, tellurium and others have been formed by environmental bacterial isolates, suggesting enzymatic redox processes. Various fungal species also reduce metal ions through quinones and/or intra- and extracellular enzymes. From many of the species that form inorganic nanoparticles, enzymes are identified in that reduce inorganic ions including as silica, chromate, cerium, selenite, selenate, tellurite, and tellurate.

For most of the enzymes identified, reduction occurs through an electron transfer utilizing the cofactors NADH or NADPH. In the case of bioremediase identified by Chowdury et al. (*JBIC J. Biol. Inorg. Chem.* 2015, 20 (5), 791) the formation of $SiO_2$ from tetraethyl orthosilicate was catalyzed through a $Zn^{2+}$ ion bound by the enzyme resulting in 25±5 nm diameter nanoparticles. An extracellular cystathione γ-lyase from *S. maltophilia*, capable of removing a sulfide from cysteine was isolated and used to make CdS quantum dots. This same enzyme was then used to produce numerous core-shell quantum dots by utilizing cysteine and/or selenocysteine. A glutathione reductase like-metalloid reductase (GRLMR) was identified (*ACS Omega* 2018, 3 (11), 14902) capable of reducing seleno-diglutathione, selenite, and selenate to amorphous SeNP.

Whereas natural evolutionary processes can result in inorganic ion redox enzymes, in vitro selections have identified peptides that can bind to and sometimes exert control over the synthesis of inorganic materials such as CdS, FePt, ZnS, $GeO_2$, $TiO_2$, CoPt, and $CaCo_3$. The pioneering works of Belcher and colleagues (*Science* 2002, 296 (5569), 892) demonstrated the use of M13 phage for the ordering of quantum dots through the identification and fusion of inorganic interacting peptides to M13's major coat protein, p8. Subsequently, this approach produced highly structured hybrid materials. Ahmad et al. (*J. Am. Chem. Soc.* 2008, 130 (1), 4) isolated 2 peptides exhibiting a catalytic ability to form crystalline $BaTiO_3$ precipitates from barium acetate and potassium bis(oxalate) oxotitanate at near neutral pH, although without any major size controlling effects. Two other sequence-unique peptides were identified by Bassindale et al. (*Chem. Commun.* 2007, 0 (28), 2956) capable of interacting with AgNPs. Ag-22 formed triangular, quadrangular, and spherical shapes while Ag-28 formed uniformly spherical NPs. Feldheim et al. (*ACS Nano* 2010, 4 (7), 3883) showed that a peptide originally isolated for binding to Germanium could exert profound effects on the formation of Ag nanostructures.

Visualization of biological systems is a difficult goal to reach. For example, crystallography proves difficult for the purity of protein required as well as discerning stoichiometric ratios and protein interfaces as opposed to crystal interfaces. Light microscopy or immunolabeling requires various levels of processing increasing difficulty and cost. Also, electron microscopy isn't easily applied because of the lack of electron density. Accordingly, other means of visualizing biological systems are needed to advance the understanding of biological structures and processes.

SUMMARY

Investigations of metal binding peptides and metal reducing enzymes represent entirely separate fields of inquiry. For the first time, the effect of a selected peptide on enzymatic nanomaterial production was investigated. A selenium nanoparticle (SeNP) binding peptide effecting enzymatic production of SeNPs was discovered. It was found that the peptide changes the SeNP sizes and distributions. However, this is only observed robustly when the peptide is genetically concatenated to the enzyme, not when the peptide is freely available in solution. More unexpectedly, a change in the enzyme's kinetic properties was observed. Based on Raman spectroscopy, the peptide binding to the SeNP through Histidine ligation was characterized.

Additionally, cloneable nanoparticles are inorganic nanoparticles produced by enzymatic scaffolds that can be genetically fused to a target protein. Upon that proteins expression and incubated with the proper inorganic salt, a NP can form for visualization in electron microscopy Accordingly, this disclosure provides a redox-active tag comprising:
  a) a reducing enzyme wherein the enzyme selectively reduces an elemental species to an element having a reduced-oxidation state; and
  b) a binding peptide wherein the binding peptide selectively binds the element;
  wherein the binding peptide is fused to the enzyme thereby forming the redox-active tag; and wherein a population of redox-active tags can form nanoparticles having a uniform size distribution.

This disclosure also provides a plasmid of a redox-active tag comprising:
  a) a first gene encoding a metal-reducing enzyme wherein the enzyme when expressed selectively reduces an oxidized metal to a metal (0) having a zero-oxidation state;
  b) deoxyribonucleic acid (DNA) encoding a metal-binding peptide wherein the binding peptide when expressed selectively binds the metal (0); and
  c) a second gene encoding a target protein;

wherein the binding peptide, enzyme and target protein are fused in the plasmid; and the plasmid can express a population of redox-active tags at the target protein in a cell.

Additionally, this disclosure provides a method for detecting cloned nanoparticles in cells comprising:

a) forming tagged cells by expressing the population of redox-active tags at the target protein in cells resulting from the plasmid described above;

b) incubating the tagged cells with a metal salt to form cloned nanoparticles via enzymatic reduction of the metal salt and retention of the metal (0) by the binding peptide wherein the cloned nanoparticles have a uniform size distribution; and c) detecting the cloned nanoparticles at the target protein in the cells.

Furthermore, this disclosure provides a method for forming cloned nanoparticles comprising:

a) fusing in a plasmid:
   i) a first gene encoding a metal-reducing enzyme wherein the enzyme when expressed selectively reduces an oxidized metal to a metal (0) having a zero-oxidation state;
   ii) deoxyribonucleic acid (DNA) encoding a metal-binding peptide wherein the binding peptide when expressed selectively binds the metal (0); and
   iii) a second gene encoding a target protein;

wherein the binding peptide, enzyme and target protein are fused in the plasmid;

b) forming tagged cells by expressing a population of redox-active tags at the target protein in the cells resulting from the plasmid; and c) incubating the tagged cells with a metal salt to form cloned nanoparticles via enzymatic reduction of the metal salt and retention of the metal (0) by the binding peptide wherein the cloned nanoparticles have a uniform size distribution.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
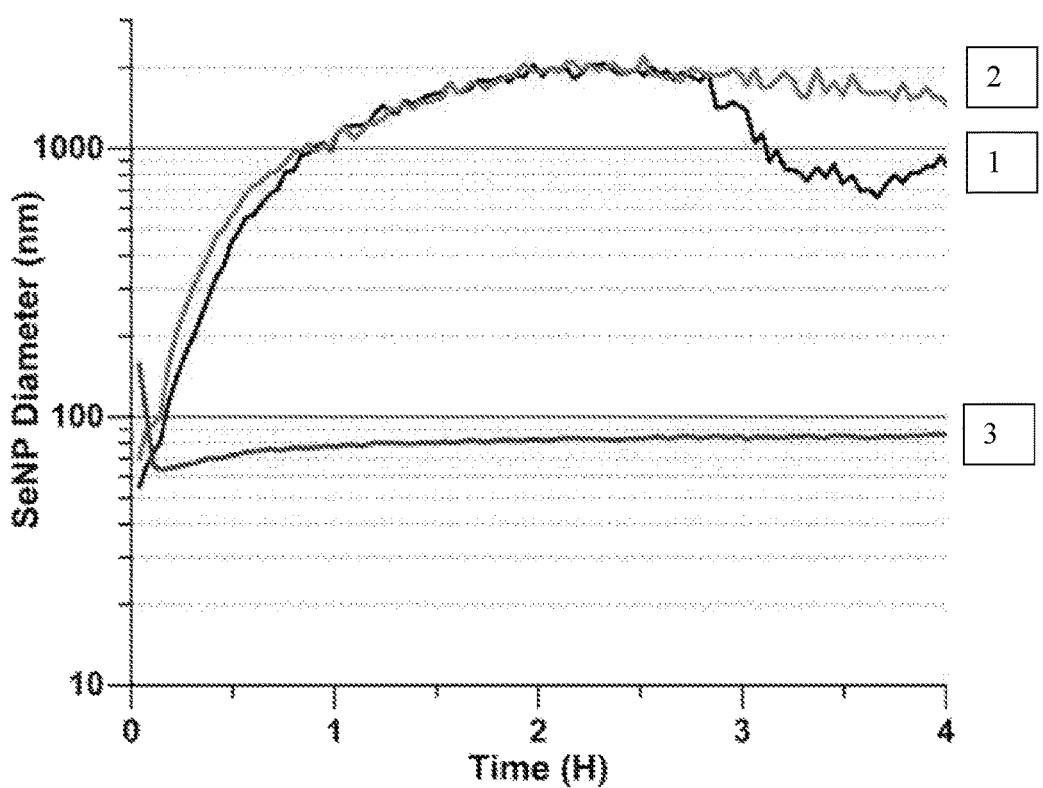
FIG. 1. Intensity based DLS data (A) comparing SeNPs produced by GRLMR (1), GRLMR with exogenous SeBP (2), and GRLMR with fused SeBP (3). (B) Cartoon representations and the resulting pictures of the reaction vessels after DLS are shown with GRLMR on top, GRLMR and exogenous SeBP in the middle, and GRLMR-SeBP represented at the bottom.
Figure 1:
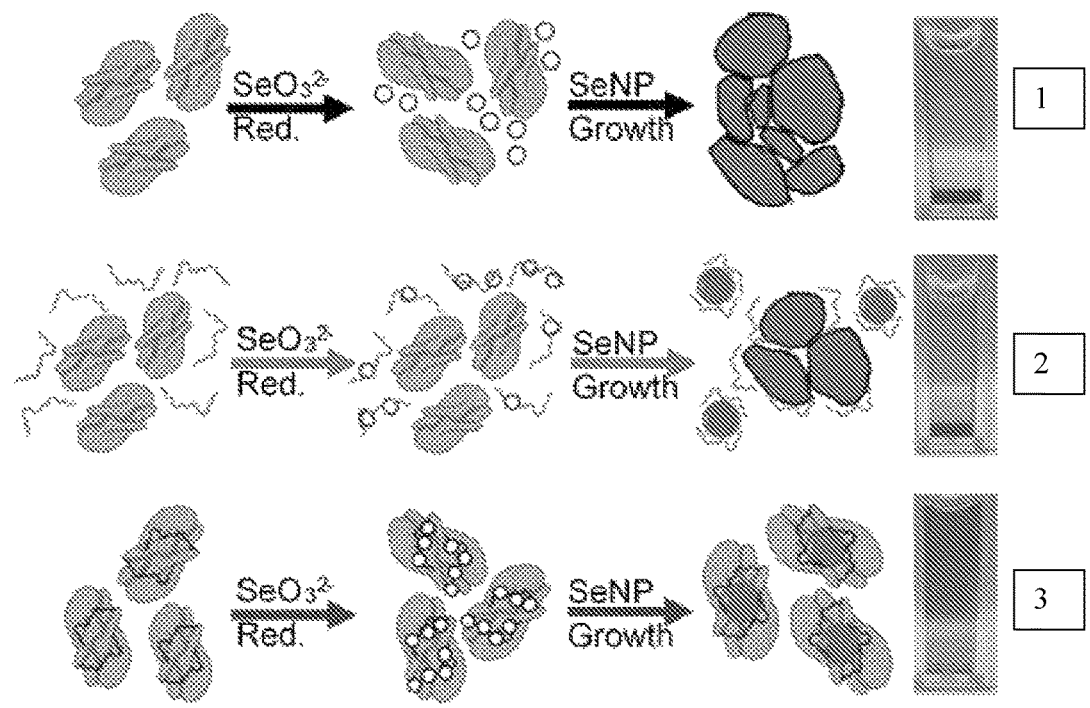

Images are made by contrast. In other words, only things that are distinguishable from their background can be observed. This is why it is difficult to see a chameleon on a leaf—there is almost no contrast. In all forms of biological imaging, whether the images are formed from illumination by X-rays, electrons, or light, many things are visible, yet many other things remain camouflaged or indistinguishable from the background. For instance, in an X-ray, it's easy to see bones, but not so easy to see muscles, fat or skin. This is also true in microscopic images, where it's often easy to see the edges of cells, but much harder to see the details inside cells. Overall, this is the contrast problem—there is very little intrinsic imaging contrast inside biological systems.

The contrast problem in biological electron microscopy (EM), especially of cells, remains daunting. For instance, there is no straightforward 'clonable contrast' analogous to fluorescent proteins used in optical microscopy.

The use of metal reducing enzymes (MREs) to produce inorganic tags for biological electron and optical microscopy (referred to here as 'Clonable Nanoparticles'). These MREs can be fused to a gene of interest, at the genetic level; like Green Fluorescent Protein (GFP). MREs can produce and retain localized inorganic quantum dots or nanoparticles to localize proteins in electron microscopy (EM), x-ray imaging and/or optical microscopy, like the way GFP can localize proteins in optical microscopy. These enzyme tags meet 3 criteria; metal reduction, particle retention, and particle size control. A Glutathione Reductase-like Metalloid Reductase (GSHRMR) isolated from *P. moraviensis* Stanleyae capable of these 3 criteria has been identified.

EM provides an image of inorganic materials at the atomic level, a resolution not yet readily obtained for biological imaging. Inorganic nanoparticles (NPs) have been used for biological EM imaging, however unlike other approaches, MREs provides a biological scaffold to produce nanoparticles in situ. MRE based tags would provide several different imaging approaches difficult or unlikely to be used otherwise: 1) placement of atomic models in cellular electron tomograms, 2) in situ cryo-EM reconstructions, and 3) deep tissue cloneable contrast.

Another highly beneficial aspect of these MRE based tags is the ability to form quantum dots (QDs) which are quantum confined NPs that have tight fluorescent profiles. QDs don't bleach allowing for extended optical observation of samples without the concern of losing observed fluorescence. Being able to combine a tag that allows for EM and optical imaging has yet to be realized until this MRE tag. To increase the versatility of this approach, other MREs are being identified that allow production of other metal NPs. The metals so far identified as affected are Se, Te, Cd, and Zn. These metals are of major interest for one or more of the following reasons: 1) metal atoms have a high electron density, 2) once added to an imaging sample the metal precursors are available for reduction by the MRE tag, 3) reduction of these metals does not readily occur within a cellular environment, 4) these metals are constituents of synthesized quantum dots.

This could be distributed as a kit with which researchers can insert a protein of interest into a plasmid that contains the MRE tag or allow for the tag to be inserted into the genome of a species at a specific location. This kit would contain a plasmid with one or more of the MREs, optimized to their studied species (i.e. *E. coli*, yeast, etc.), a master mix for the insertion of the desired gene into the plasmid, and possible solutions of metal salt precursors for the eventual NP formations.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "elemental species" refers to any element or isotope of the periodic table at any known oxidation state.

The term "target protein" is used herein as a term commonly understood by ordinary persons skilled in the art. The term generally refers to functional biomolecules that can be addressed and controlled by biologically active compounds. Target proteins control the action and the kinetic behavior of drugs and other biomolecules within the organism.

The term "fused" or "fusion" relates to fusion proteins and is used herein as a term commonly understood by ordinary persons skilled in the art. Fusion proteins are created through the joining of two or more genes that originally coded for separate proteins. Translation of the fusion gene results in polypeptides with functional properties derived from each of the original proteins. Recombinant fusion proteins are created artificially by recombinant DNA technology for use in biological research or therapeutics.

The term "tag" relates to protein tags and is used herein as a term commonly understood by ordinary persons skilled in the art. Protein tags are peptide sequences genetically grafted onto a recombinant protein. Tags are attached to proteins for various purposes. For example, fluorescence tags are used to give visual readout on a protein. Green fluorescent protein (GFP) and its variants are the most commonly used fluorescence tags. Tags described in this disclosure are redox-active tags that form nanoparticles which can be visualized by electron microscopy and the like.

The term "fix" or "fixation" relates to the preservation of biological cells or tissues from decay and is used herein as a term commonly understood by ordinary persons skilled in the art. Fixation terminates any ongoing biochemical reactions and may also increase the treated cells' mechanical strength or stability. This allows the investigation of the cells' structure and biological processes.

Embodiments of the Invention

This disclosure provides a redox-active tag comprising:
a) a reducing enzyme wherein the enzyme selectively reduces an elemental species to an element having a reduced-oxidation state; and
b) a binding peptide wherein the binding peptide selectively binds the element;
wherein the binding peptide is fused to the enzyme thereby forming the redox-active tag; and wherein a population of redox-active tags can form nanoparticles having a uniform size distribution.

In various embodiments, the redox-active tag is fused to a target protein. In additional embodiments, the reducing enzyme selectively reduces a metal, metalloid, chalcogen, semimetal, metal ion, cation, or anion, or non-metal. In other embodiments, the reducing enzyme selectively reduces an oxidized metal to a metal (0) having a zero-oxidation state.

In further embodiments, the reducing enzyme selectively reduces an oxidized form of selenium, tellurium, cadmium, magnesium, iron, platinum, germanium, titanium, cobalt, silver, gold, zinc, arsenic, cerium, bismuth, silicon, tin, lead, copper, nickel, aluminum, indium, or a combination thereof to an oxidation state of zero. In some embodiments, the reducing enzyme selectively reduces sulfur. In some embodiments, the reducing enzyme selectively reduces a salt of selenium to selenium (0) metal. In other embodiments, the reducing enzyme is glutathione reductase-like metalloid reductase (GRLMR), mycothione reductase, cytochrome b5 reductase, glutathione reductase, bioremediase, or silicatein. In some embodiments the GRLMR is dimeric or monomeric.

In various embodiments, the binding peptide selectively binds a metal, metalloid, chalcogen, semimetal, metal ion, cation, or anion, or non-metal. In some embodiments, the binding peptide selectively binds a metal (0) having a zero-oxidation state. In other embodiments, the binding peptide selectively binds selenium (0), tellurium (0), cadmium (0), magnesium (0), iron (0), platinum (0), germanium (0), titanium (0), cobalt (0), silver (0), gold (0), zinc (0), CdSe, CdTe, or CdS. In other embodiments, the binding peptide selectively binds selenium (0). In additional embodiments, the binding peptide comprises a dodecapeptide that selectively binds and retains a metal (0) via metal-binding moieties.

In various embodiments, the nanoparticles are metal nanoparticles when formed. In additional embodiments, the nanoparticles when formed have a diameter of about 1 nm to about 250 nm. In other various embodiments, the diameter is about 5 nm to about 50 nm, about 50 nm to about 100 nm, about 100 nm to about 150 nm, about 150 nm to about 200 nm, or about 200 nm to about 250 nm. In further embodiments, the nanoparticles when formed have a uniform size distribution characterized by a root mean square (rms) deviation in diameter of less than about 25%. In some embodiments, the rms deviation is less than about 10%. In other embodiments, the rms deviation is about 5% to about 10%, or about 10% to about 20%.

In various additional embodiments, the (metal/metalloid) reductase activity, $V_o$, of the reducing enzyme moiety of the redox-active tag is increased at least 10% relative to the (metal/metalloid) reductase activity of a corresponding reducing enzyme that is not fused to the binding peptide. In other embodiments, the reductase activity is increased by about 5% to about 15%, about 15% to about 25%, about 25% to about 40%, about 40% to about 60%, about 60% to about 80%, about 80% to about 99%, or more than 100%.

Additionally, this disclosure provides a plasmid of a redox-active tag comprising:
a) a first gene encoding a metal-reducing enzyme wherein the enzyme when expressed selectively reduces an oxidized metal to a metal (0) having a zero-oxidation state;
b) deoxyribonucleic acid (DNA) encoding a metal-binding peptide wherein the binding peptide when expressed selectively binds the metal (0); and
c) a second gene encoding a target protein;
wherein the binding peptide, enzyme and target protein are fused in the plasmid; and
the plasmid can express a population of redox-active tags at the target protein in a cell.

In various embodiments, the population of redox-active tags can form metal nanoparticles of uniform size distribution when the cell is incubated with a metal salt, or when the cell is exposed to a metal salt after a cell-fixation step.

This disclosure also provides a method for detecting cloned nanoparticles in cells comprising:
a) forming tagged cells by expressing the population of redox-active tags at the target protein in cells resulting from the plasmid herein;
b) incubating the tagged cells (pre- or post-fixation) with a metal salt to form cloned nanoparticles via enzymatic reduction of the metal salt and retention of the metal (0) by the binding peptide wherein the cloned nanoparticles have a uniform size distribution; and
c) detecting the cloned nanoparticles at the target protein in the cells.

In various other embodiments, the metal-reducing enzyme is glutathione reductase-like metalloid reductase (GRLMR). In some embodiments, the GRLMR reduces a salt of selenium to selenium (0) metal. In other embodiments, the metal-binding peptide comprises a dodecapeptide that selectively binds and retains the selenium (0) via histidine moieties. In various additional embodiments, the binding peptide comprises a peptide that retains a metal or metalloid or via the binding moieties of the peptide.

In additional embodiments, the cloned nanoparticles have a diameter of about 1 nm to about 250 nm. In other embodiments, the uniform size distribution of the cloned nanoparticles is characterized by a root mean square (rms) deviation in diameter of less than about 25%. In further embodiments, detecting the cloned nanoparticles at the target protein in the cells is performed by scanning electron microscopy (SEM), transmission electron microscopy (TES) or optical microscopy.

Also, this disclosure provides a method for forming cloned nanoparticles comprising:
a) fusing in a plasmid:
i) a first gene encoding a metal-reducing enzyme wherein the enzyme when expressed selectively reduces an oxidized metal to a metal (0) having a zero-oxidation state;
ii) deoxyribonucleic acid (DNA) encoding a metal-binding peptide wherein the binding peptide when expressed selectively binds the metal (0); and
iii) a second gene encoding a target protein;
wherein the binding peptide, enzyme and target protein are fused in the plasmid;
b) forming tagged cells by expressing a population of redox-active tags at the target protein in the cells resulting from the plasmid; and
c) incubating the tagged cells (pre- or post-fixation) with a metal salt to form cloned nanoparticles via enzymatic reduction of the metal salt and retention of the metal (0) by the binding peptide wherein the cloned nanoparticles have a uniform size distribution.

In some embodiments, the cloned nanoparticles have a diameter of about 1 nm to about 250 nm. In other embodiments, the uniform size distribution of the cloned nanoparticles is characterized by a root mean square (rms) deviation in diameter of less than about 25%. In one embodiment, the target protein is a protein from a bacterium or a virus.

In further embodiments, this disclosure provides a redox-active tag comprising:
a) a metal-reducing enzyme wherein the enzyme selectively reduces an oxidized metal to a metal (0) having a zero-oxidation state; and
b) a metal-binding protein wherein the binding protein selectively binds the metal (0);
wherein the binding protein is fused to the enzyme thereby forming the redox-active tag; and wherein a population of redox-active tags can form metal nanoparticles having a uniform size distribution.

Results and Discussion

Figure 8:
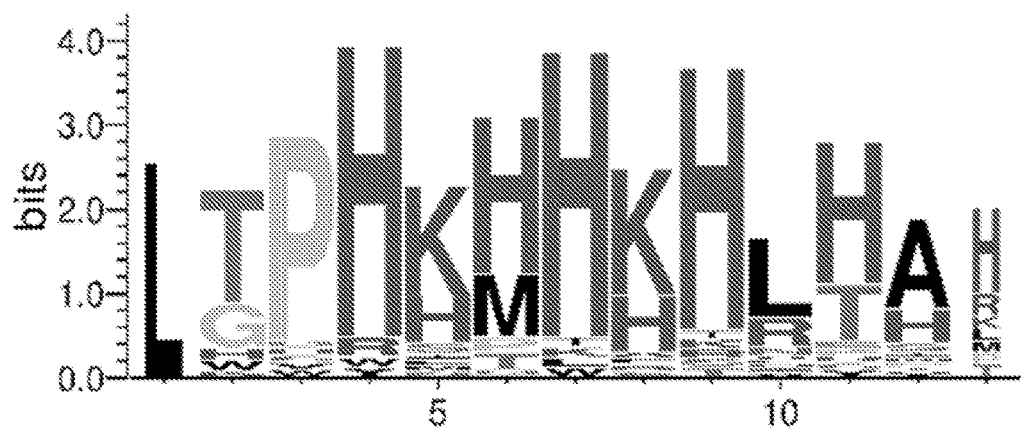
FIG. 8. Frequency plot produced after sequencing 33 individually infected colonies. Letter width indicates the number of residues at the peptide position upon alignment. Height correlates to the frequency of a specific residue at a specific position.
Figure 9:
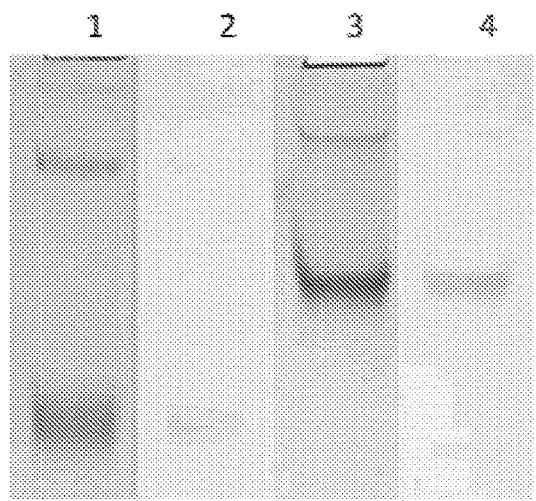
FIG. 9. Native Page of GRLMR stained with Coomassie (1) or $SeO_3^{2-}$ (2) and GRLMR-SeBP stained with Coomassie (3) or $SeO_3^{2-}$ (4).

A SeNP binding dodecapeptide, SeBP, was isolated from a New England Biolabs PhD phage display library following the manufacturer's protocol (see Examples). DNA encoding SeBP was concatenated to the C-terminus of GRLMR by outward PCR (GRLMR-SeBP). Presence of the SeBP was confirmed through sequencing and Native-PAGE (FIGS. 8 & 9). GRLMR-SeBP was expressed as previously described using T7 Express BL21 (DE3) *E. coli* (NEB Catalog #C3013I). After induction with 1 mM IPTG, the 1 L growth culture was supplemented with 1 μM of $HNaSeO_3$ and grown overnight at 37° C. and 225 RPM. Supplementing with selenite increased the yield of the enzyme considerably by mitigating selenium deficiency in the culture due to scavenging of selenium by the expressed GRLMR-SeBP. GRLMR-SeBP was then purified from lysed cells with an Ni-NTA column.

Prior work revealed that in the presence of sufficient concentrations of $SeO_3^{2-}$ and NADPH, the enzymatic activity results in precipitation of red-selenium (*Nanoscale* 2015, 7 (41), 17320). This activity is depicted in FIG. 1, as the dynamic light scattering (DLS) trace (1) in panel A and as the top cartoon and cuvette photo in panel B. The ultimate enzymatic product in conditions of excess reactants are micron sized particles that collect at the bottom of the reaction vessel.

Figure 10A:
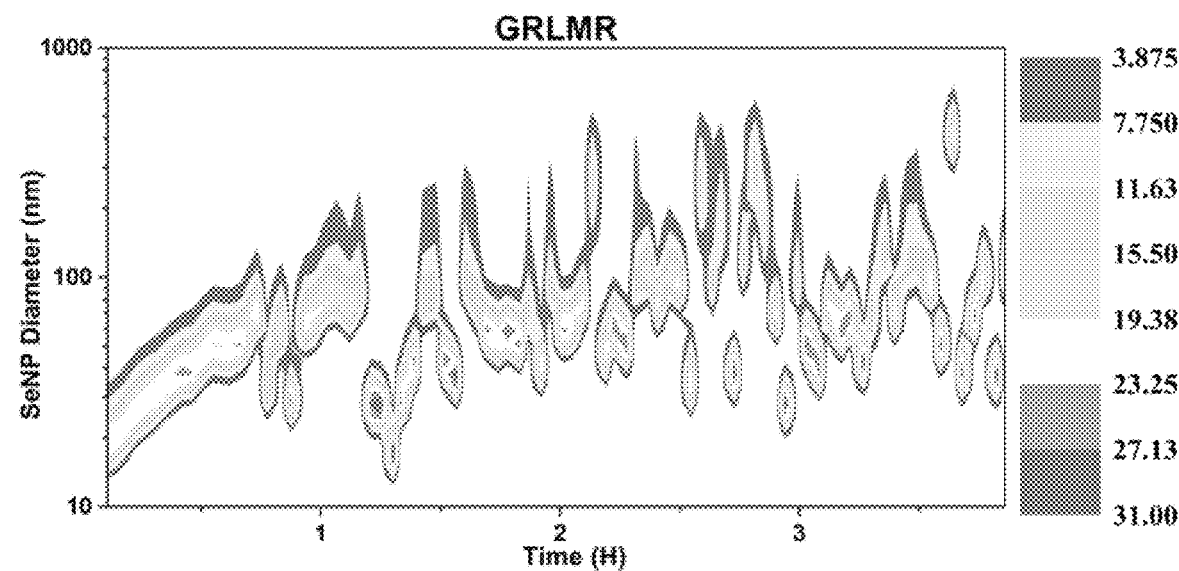
FIG. 10A-C. Dynamic Light Scattering Size Data: Contour maps following population size of SeNPs over time in DLS.
Figure 10B:
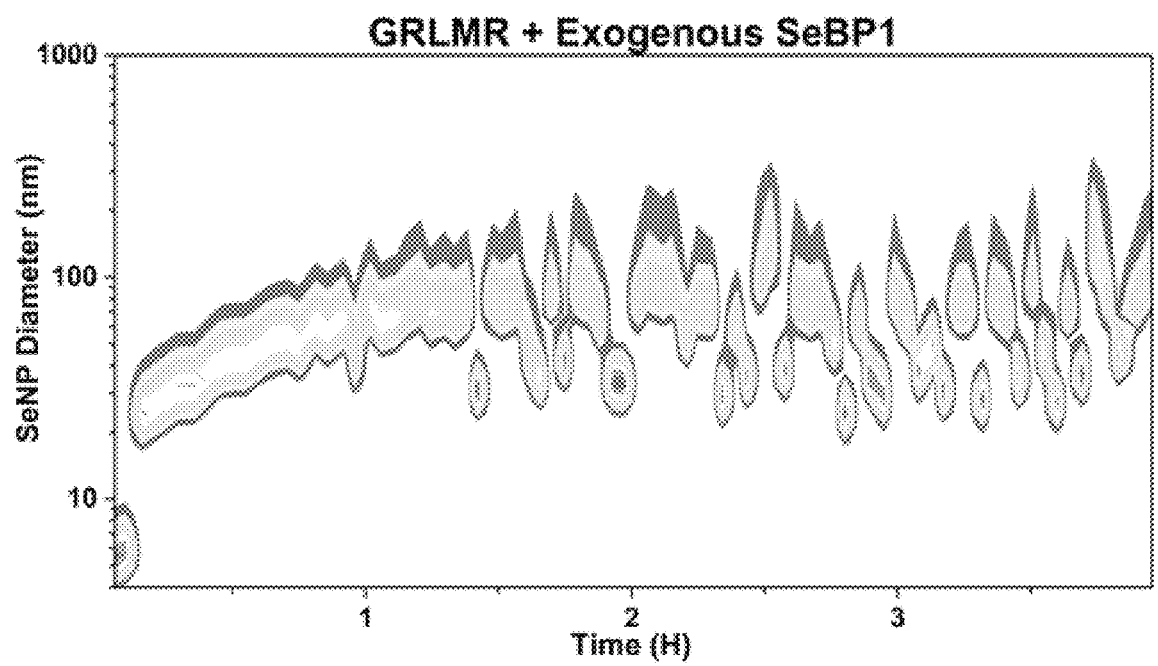
Figure 10C:
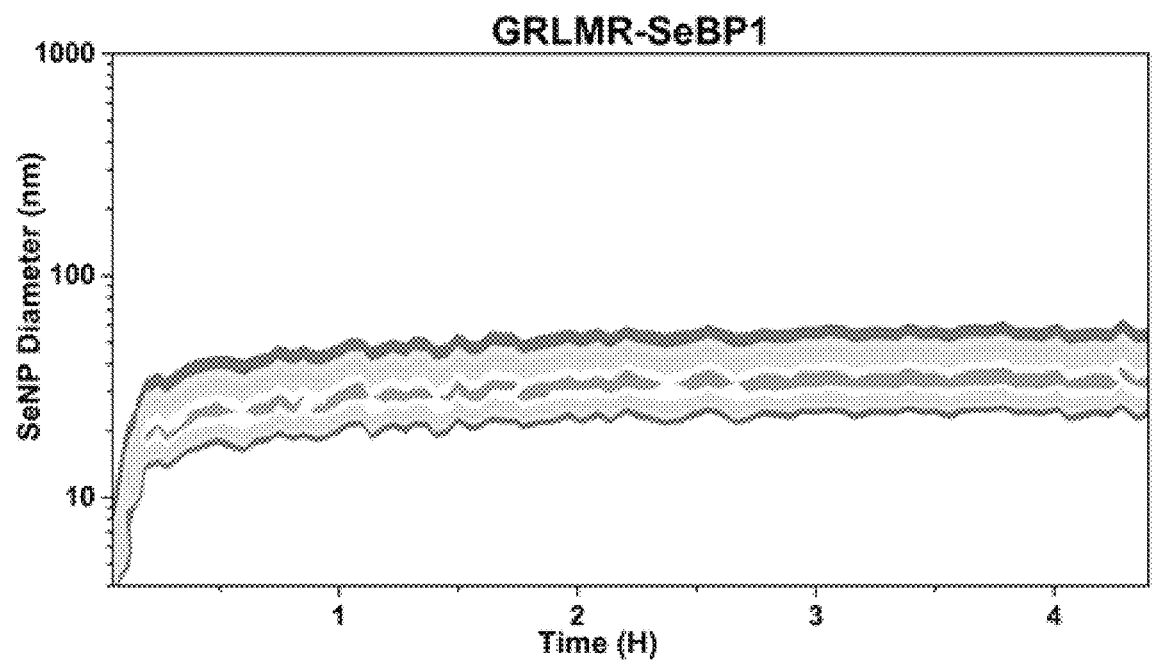

When SeBP is concatenated to GRLMR, the product size and distribution changes dramatically. The trace (3) in FIG. 1, panel A shows that the Se$^0$ product size is dramatically restricted to a size of ~85 nm, several orders of magnitude smaller than the micron sized particles that result in the absence of concatenated SeBP. The DLS data shown in FIG. 1, panel A is intensity based which skews to larger products. When the data was converted to number based in order to better represent the population, the resulting SeNPs were even smaller at ~35 nm (FIG. 10). Consistent with SeNP growth-arrest at a sub-100 nm diameter, it was observed that the reaction solution is red in color, with no precipitate forming at the bottom of the reaction vessel.

Interestingly, for the size-control effect to be observed, it is compulsory that the peptide is concatenated to the enzyme. If the peptide is simply added exogenously to the solution, no-such limitation to Se$^0$ product size was observed, as shown in the trace (2) of FIG. 1, panel A and the middle cartoon of panel B.

Figure 2:
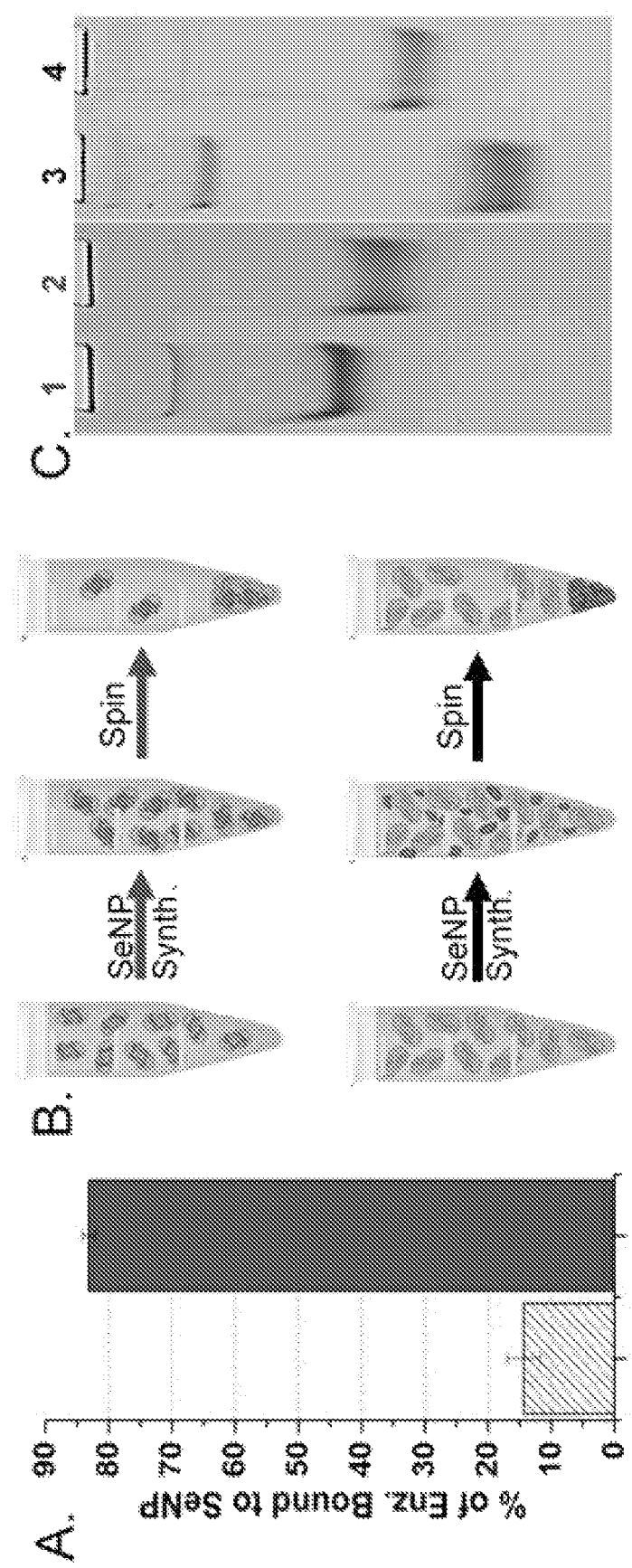
FIG. 2. (A) Soluble GRLMR (diagonal stripe) and GRLMR-SeBP1 (solid bar), determined by Bradford assay, present after removal of enzyme coated SeNPs through centrifugation. (B) Diagram representing the removal of the GRLMR-SeBP1 (top) associated to SeNP while GRLMR (bottom) remains largely unassociated and therefore remains in the supernatant after centrifugation. (C) Native PAGE gel of unreacted GRLMR-SeBP (Lane 1) and GRLMR (Lane 3) and soluble GRLMR-SeBP (Lane 2) and GRLMR (Lane 4) post-SeNP synthesis.

The dramatically smaller hydrodynamic radius of SeNPs produced by GRLMR-SeBP implies a stable non-covalent binding interaction between the SeNP reaction product and the peptide-modified enzyme. To determine if GRLMR-SeBP is stably associated with SeNPs, a pull-down assay was executed as depicted in FIG. 2. The basis of the pull-down assay is that the density of SeNPs allows them to be centrifugally removed from suspension, accompanied by any associated enzyme. This assay shows 83.1±1.0% and 14.4±2.6% of GRLMR-SeBP and GRLMR, respectively, associated with the SeNP fraction, as shown in FIG. 2, panel A. It is possible that this assay under-estimates the amount of enzyme associated with particles, as sufficiently small SeNPs may not be centrifugally removed at the speeds used here, yet remain enzyme-associated, as depicted in FIG. 2, panel B and supported by the data in FIG. 2, panel C (vide infra).

Figure 11:
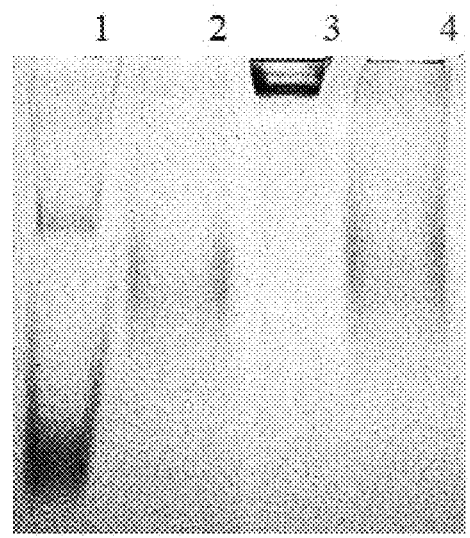
FIG. 11. A pH 6.6 native PAGE gel with unreacted GRLMR (1), reacted GRLMR (2), unreacted GRLMR-SeBP (3), and reacted GRLMR-SeBP (4).

A native/nondenaturing Polyacrylamide Gel Electrophoresis (native-PAGE) experiment (FIG. 2, panel C) suggests qualitatively that indeed a larger fraction than 83.1±1.0% of GRLMR-SeBP is bound to SeNPs. The gel mobility in this pH 8.3 matrix of GRLMR-SeBP and GRLMR are shown in lanes 1 and 3, respectively. The addition of 5 His and 2 Lys residues in the SeBP concatenation that produces GRLMR-SeBP provokes a notable gel-shift relative to native GRLMR, which is attributed to a substantial change in net-charge to a more positive value. The presence of the SeBP on GRLMR increases the calculated pI from 6.06 to 6.37. To further accentuate the charge difference between GRLMR and GRLMR-SeBP, a pH 6.6 native-PAGE gel was run following the buffer solution described by McLellan (*Anal. Biochem.* 1982, 126 (1), 94). GRLMR-SeBP only slightly migrates into the gel indicating a pI closer to 6.6 (FIG. 11).

Lanes 2 and 4 show GRLMR-SeBP and GRLMR, respectively, after they are used in an enzymatic SeNP synthesis and dialyzed into milliQ water to remove excess salts from the reaction. For each reaction, a gel-shift relative to unreacted enzyme was observed, which is attributed to the enzyme-SeNP complexation. In other words, SeNPs are bound to the enzyme, which alters its electrophoretic mobility. In the case of reacted GRLMR-SeBP/SeNP complexes, an electrophoretic mobility shift toward a lower mass-to-charge product was observed. The shift to the SeNP binding is attributed specifically to the SeBP component, thereby neutralizing the charge added to the GRLMR-SeBP by the SeBP concatenation. In the case of reacted GRLMR, the electrophoretic mobility shift is toward a higher mass-to-charge product, which is attributed to the increased mass of GRLMR-SeNP relative to GRLMR. This provides strong evidence that the SeNPs bind to the SeBP. Charge neutralization of the SeBP fragment coupled with the mass change of SeNP binding to GRLMR gives both enzyme-SeNP products a similar gel-mobility.

Figure 3:
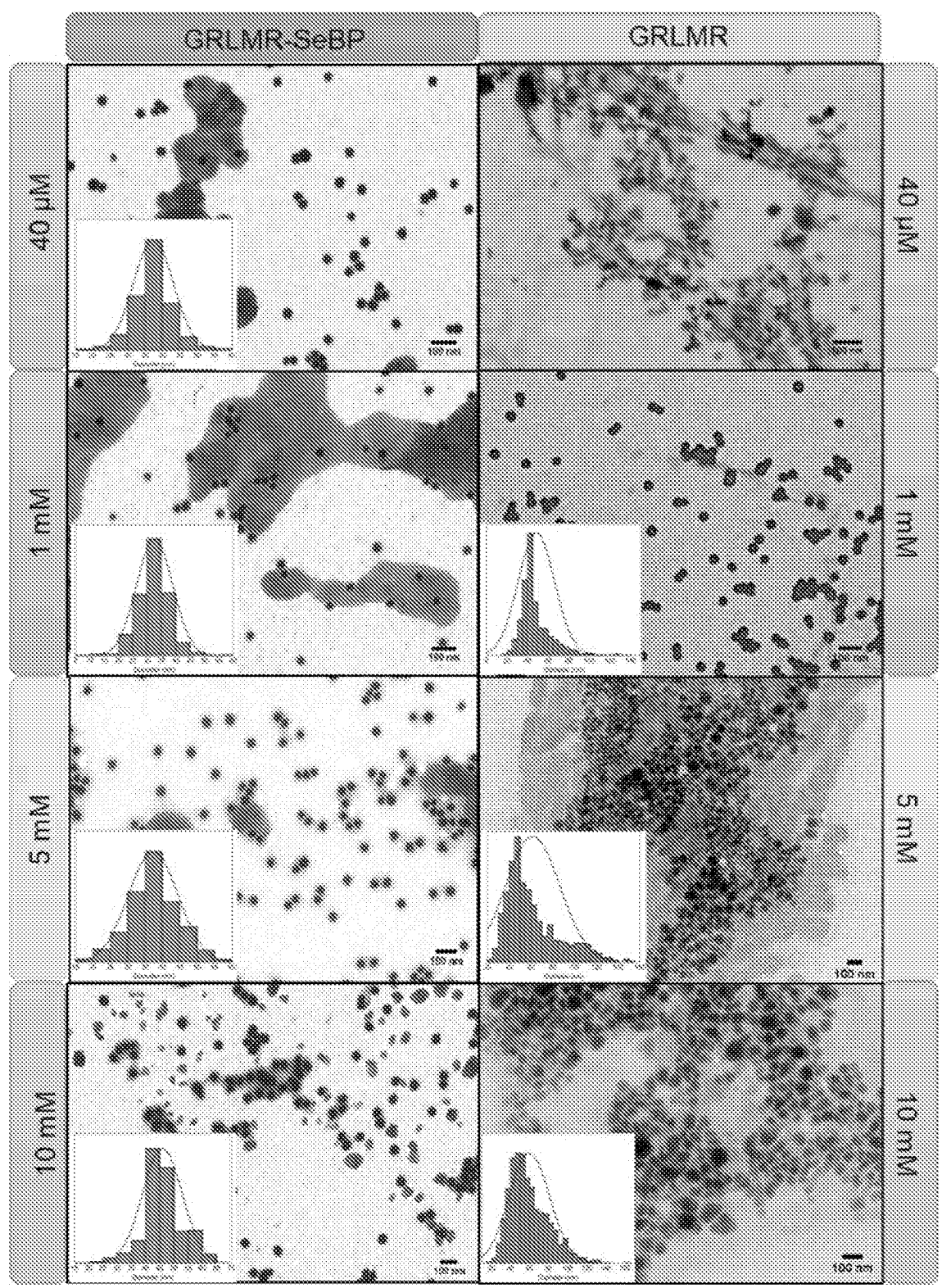
FIG. 3. SEM images of SeNPs produced by either GRLMR-SeBP (left column) or GRLMR (right column). Rows correspond to the concentrations of $SeO_3^{2-}$ used in the reactions.

The DLS data (vide supra) implies substantial difference in Se$^0$ product size which depends upon the presence or absence of concatenated SeBP. The enzymatic Se$^0$ products by Scanning electron microscopy (SEM) was examined. As observed previously that SeO$_3^{2-}$ precursor concentrations had a strong influence on resultant SeNP size, the enzymatic products with SeO$_3^{2-}$ concentrations ranging from 40 μM to 10 mM was therefore examined. NADPH was present in excess except for samples containing 10 mM SeO$_3^{2-}$. GRLMR-SeBP produced SeNPs of diameter 37.38±5.75 nm, 32.60±6.29 nm, 37.34±7.12 nm, and 45.89±6.98 nm when the reactions contained 40 μM, 1 mM, 5 mM, and 10 mM HNaSeO$_3$, respectively (FIG. 3, left column). Thus, at the lower three 'physiological-like' concentrations of SeO$_3^{2-}$, the particles were indistinguishable within measurement error. In contrast, GRLMR sans SeBP produces SeNPs that are larger, more polydisperse, and more prone to aggregation. GRLMR produced SeNPs of diameter 48.48±17.63 nm, 61.59±24.99 nm, and 59.92±21.19 nm at SeO$_3^{2-}$ concentrations of 1 mM, 5 mM, and 10 mM, respectively (FIG. 3, right column). The diameters of particles produced by GRLMR at 40 μM could not be measured satisfactorily, therefore a representative micrograph is shown, implying that the resultant particles are much smaller than at higher concentrations.

Overall, the SEM images show that GRLMR-SeBP produces spherical, well-dispersed products of a narrow size range independent of SeO$_3^{2-}$ concentration. This contrasts with GRLMR, wherein the SeNPs are of a much wider size range, not as apparently spherical, and prone to aggregation (consistent with the DLS measurements). Notably, when GRLMR was used to make SeNP products for these SEM experiments, precipitates were visible in the reaction vessels. Precipitation of larger particles and/or aggregates may have excluded larger materials from the SEM analysis, biasing results toward measuring smaller Se$^0$ products.

Figure 4:
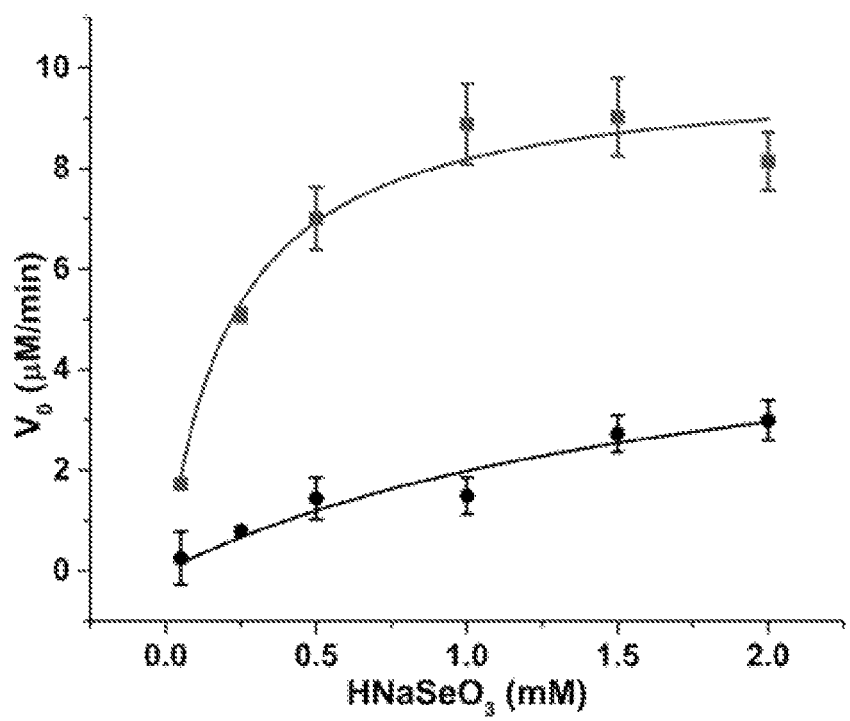
FIG. 4. $V_0$ plotted against substrate concentration of GRLMR-SeBP (■) and GRLMR (•) comparing (A) $HNaSeO_3$ and (B) GSSG.
Figure 4:
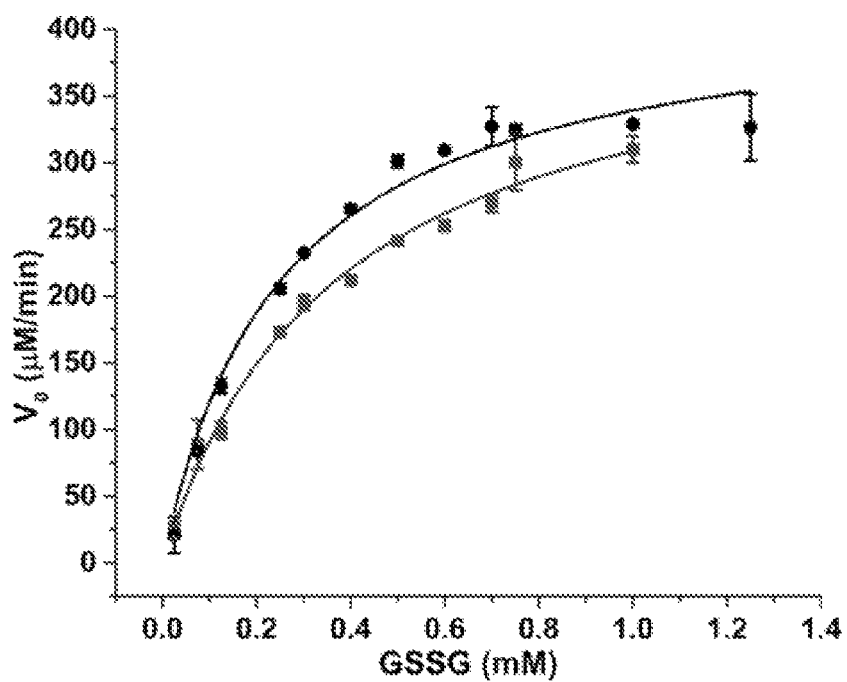

Because of the dramatic difference in SeBP size, morphology and aggregation state that depends on SeBP concatenation to GRLMR, whether this concatenation also alters the kinetic properties of the enzyme was investigated. To explore this possibility, NADPH concentrations were monitored spectroscopically during GRLMR enzymatic reactions to establish fundamental enzymatic kinetics in the presence and absence of the peptide. FIG. 4 depicts the plots of $V_0$s attained by the GRLMR with and without SeBP over a range of substrate concentrations.

The activities of GRLMR and GRLMR-SeBP, as judged by $K_M$ and $k_{cat}$ values, are markedly different when HNaSeO$_3$ is used as the substrate (FIG. 4, panel A). $K_M$ and $k_{cat}$ for both GRLMR-SeBP and GRLMR are shown in Table 1 against the different substrates HNaSeO$_3$ and GSSG. The $K_M$ of GRLMR-SeBP (0.217±0.057 mM) decreased compared to GRLMR (1.921±1.279 mM), indicating a more favorable enzyme-substrate complex. Measurements for $k_{cat}$ were 40.316±2.486 min$^{-1}$ and 22.823±8.839 min$^{-1}$ for GRLMR-SeBP and GRLMR, respectively, indicating the peptide modification results in a faster enzyme for the reduction of SeO$_3^{2-}$.

TABLE 1

Kinetics values $K_M$ and $k_{cat}$ for GRLMR-SeBP1 and GRLMR for the substrates HNaSeO₃ and GSSG.

|  | HNaSeO₃ | | GSSG | |
| --- | --- | --- | --- | --- |
|  | GRLMR-SeBP | GRLMR | GRLMR-SeBP | GRLMR |
| $K_M$ (mM) | 0.217 ± 0.057 | 1.921 ± 1.279 | 0.365 ± 0.043 | 0.253 ± 0.033 |
| $K_{cat}$ (min⁻¹) | 40.316 ± 2.486 | 22.823 ± 8.839 | 14784 ± 720 | 14498 ± 624 |

The differences in activity indicated by these kinetic experiments, notably, are also reflected in the SEM examination of enzymatic product (FIG. 3, vide supra). Specifically, at the lowest concentrations of $SeO_3^{2-}$ (40 μM) no enzymatic product for GRLMR was observed but was observed for GRLMR-SeBP. At higher concentrations of HNaSeO₃ (10-40 mM) both GRLMR-SeBP and GRLMR had the same overall activity within error, and both enzymes produce abundant nanoparticle product.

In the reduction of GSSG, the $k_{cat}$ for the two enzymes was unaffected by the presence of the SeBP as both values were within error of each other. These results indicate that the presence of SeBP on GRLMR does not hinder native function of the enzyme but does increase the enzymes ability to reduce a secondary substrate, $SeO_3^{2-}$. It was hypothesized that some of the increased activity of GRLMR-SeBP arises from the peptide introducing 5 positively charged residues proximal (34 Å) to the enzyme active site. The introduction of these residues results in a favorable charge-charge interaction with the negatively charged $SeO_3^{2-}$ anions and may allow for a higher effective concentration of the substrate near the active site.

Figure 5:
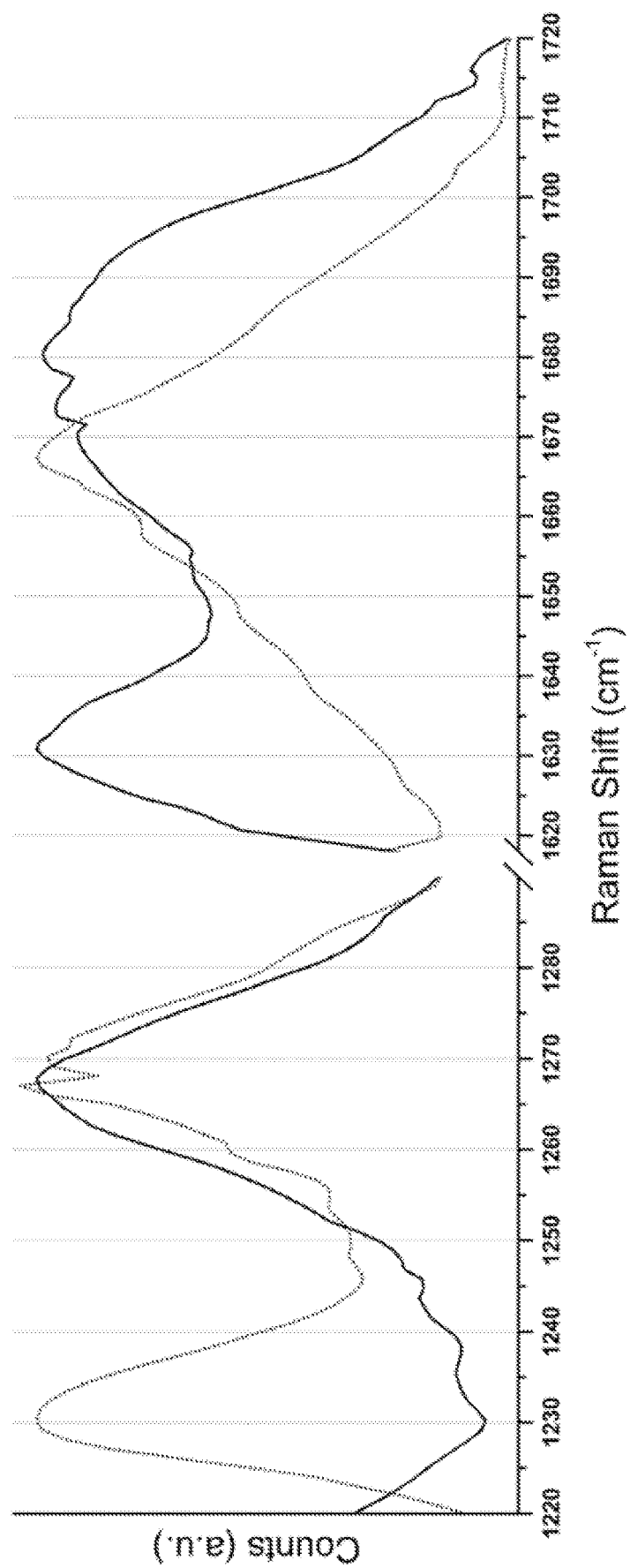
FIG. 5. Raman spectra of bound (dotted) and unbound (solid) SeBP. The peak at ~1230 $cm^{-1}$ represents an approximate assignment depicting the shift of the amide III mode to a β-sheet like structure when bound to the surface of the particle. The broad peak seen at 1680 $cm^{-1}$ indicates a random or α-helical structure of the SeBP backbone when SeNP is omitted from the sample.

Raman Spectroscopy allows structural insight into the nature of the interaction between SeBP and the SeNP surface. FIG. 5 shows an overlay of the Raman spectra of the peptide in the presence and absence of SeNPs, where the large differences in the spectra suggest a substantial interaction between peptide and nanoparticle. These spectral changes were interpreted in the presence of SeNPs as arising from two changes in the peptide: First, a change in the peptide backbone conformation; Second, multiple changes to the ligation environment of the imidazole rings of the histidine residues in the peptide.

Changes in peptide backbone conformation are ascertained in Raman spectra from the so-called Amide I, Amide II and Amide III vibrational modes. This corresponds to complex amide related vibrational modes in the peptide backbone. The amide I backbone mode is located in the 1600-1700 cm⁻¹ region. This mode is considerably influenced by transition dipole coupling, which describes the conformational dependence of the dipole interaction energy on spatial separation and orientation. The amide III mode is located in the 1200-1320 cm⁻¹ region and is also sensitive to structural rearrangement.

The amide I mode is in the 1650-1710 cm⁻¹ region as shown in FIG. 5. The broadness and location of peak corresponding to the amide I mode in the absence of SeNPs is suggestive of a disordered backbone structure (FIG. 5, right panel, solid trace). In the presence of SeNPs, the peak corresponding to the amide I mode narrows and downshifts to 1667 cm⁻¹, suggestive of a β-sheet type backbone structure (FIG. 5, dashed trace). This assignment of a change in backbone structure from disordered to β-sheet-like after SeNP binding interaction is also suggested in the amide III mode.

The amide III mode is in the 1200-1320 cm⁻¹ region as shown in FIG. 5, left panel and when unbound the mode may be hidden behind the His modes centered at 1268 cm⁻¹ (FIG. 5, solid trace). An amide III mode centered about 1260 cm⁻¹ suggests an unordered structure, and one that is centered at 1265 cm⁻¹ is suggestive of either an α-helix or a polyproline II (PPII) type structure. The presence of PPII structure is likely, since the peptide contains a Pro residue, which is the cause of this structure type. Furthermore, the presence of a proline makes helical structure unlikely in a dodecapeptide. Upon binding to an NP, the amide III mode downshifts to 1230 cm⁻¹, which also corresponds to a β-sheet structure.

In addition to the evidence for an ordering in backbone structure that is induced by the presence of SeNPs, evidence showed binding of the SeNP to the peptide is driven by interactions with the imidazole rings of the 5 His residues in the peptide. Imidazoles are well-known to coordinate with metal ions. In the context of Raman spectra, tautomer markers in the 900-1630 cm⁻¹ region are used to identify His-metal binding.

Figure 6A:
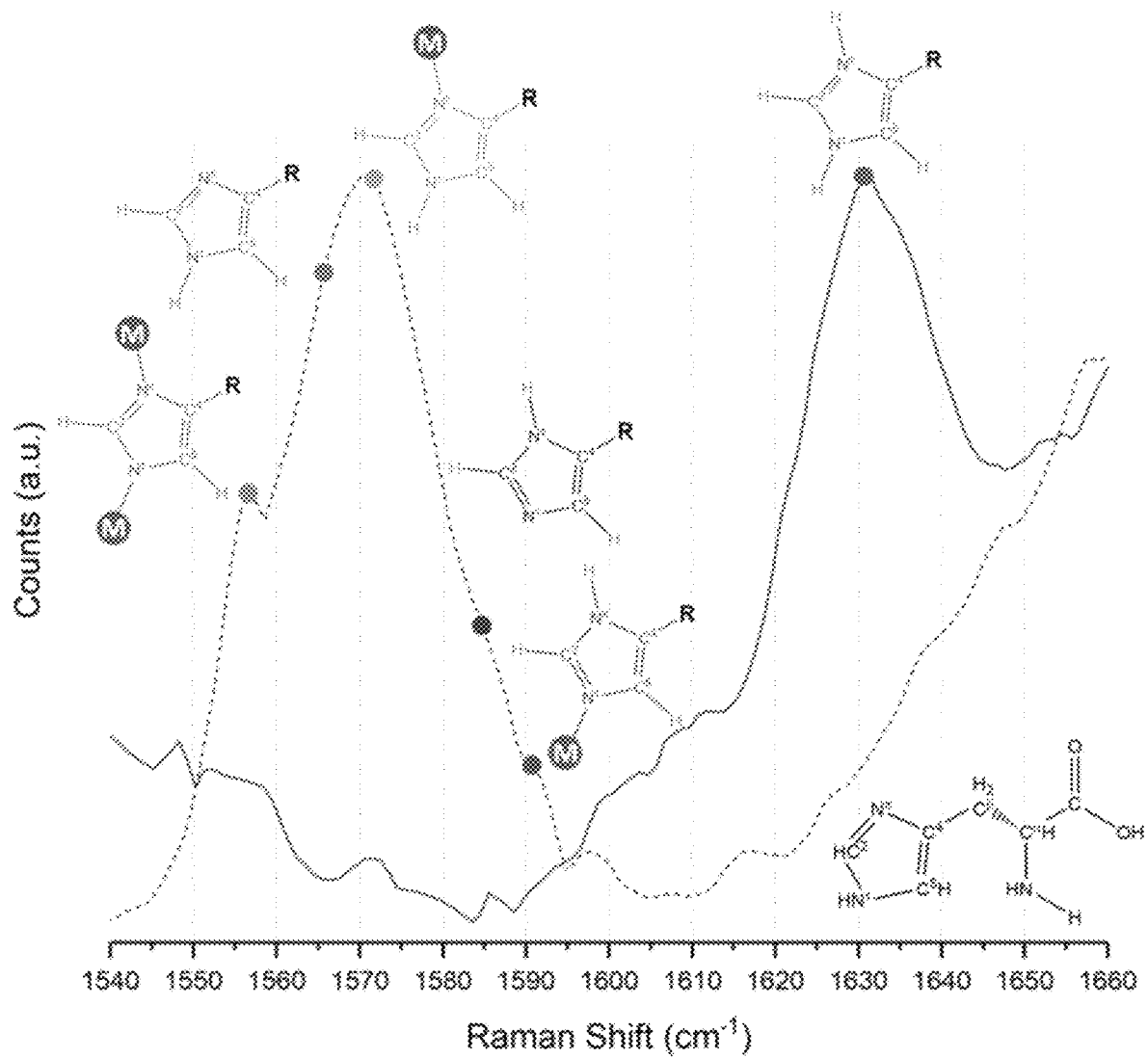
FIG. 6A-B. Raman Spectra of SeBP and SeBP/SeNP: (A) Traces of SeBP (solid) and SeBP/SeNP (dashed) from FIG. 5, expanded to the 1540-1660 $cm^{-1}$ region to show the relevant His modes described. The dots nearest the structure represents each shift shown. Histidine is represented in the lower right corner. (B) Traces of SeBP (solid) and SeBP/SeNP (dashed), expanded to the 1240-1300 $cm^{-1}$ region to show the relevant His modes described. The dots nearest the structure represents each shift shown.
Figure 6B:
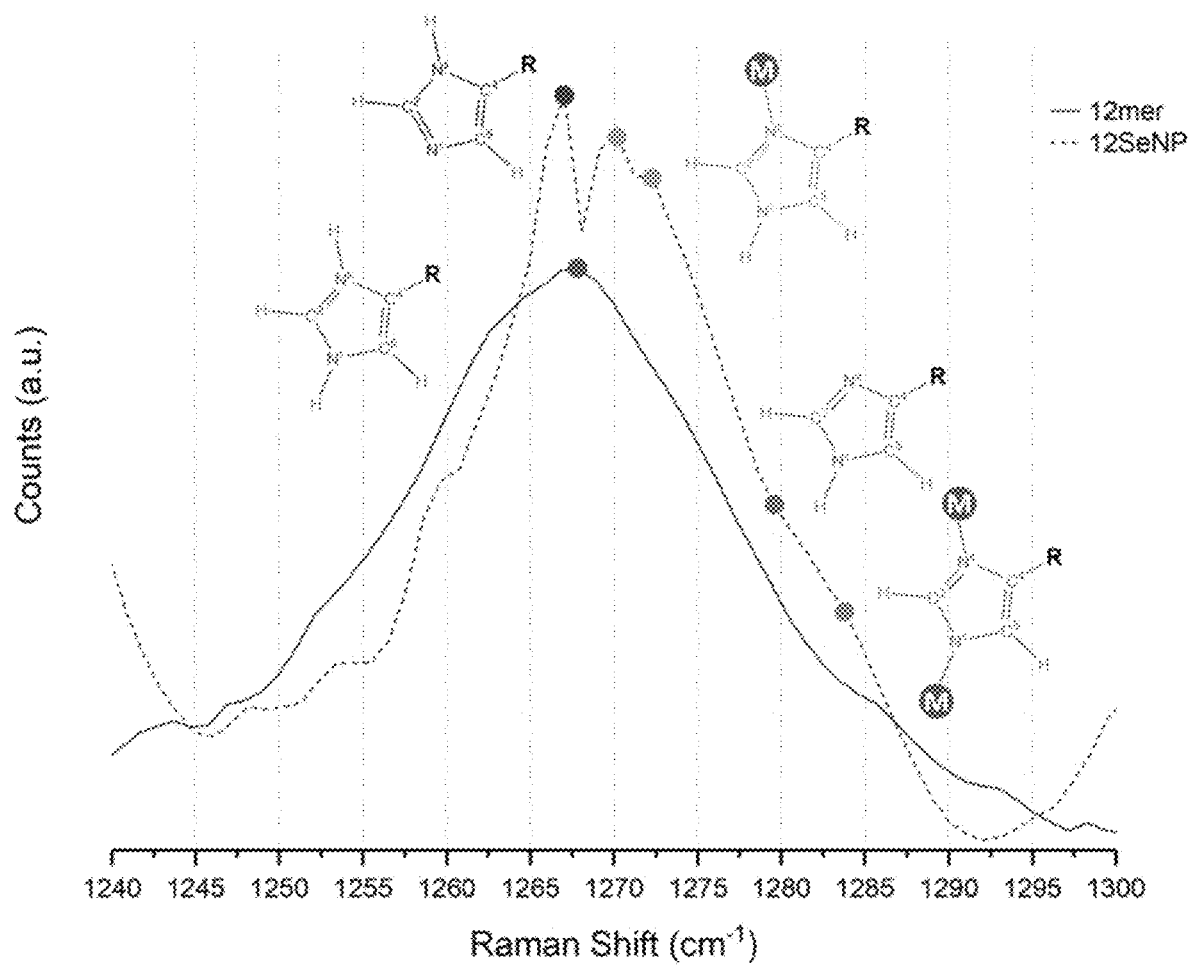

By convention, each atom within the imidazole ring of His is labeled as shown in the Lewis diagram of Histidine shown as an inset in FIG. 6. Vibrations arising from bonds between nitrogen and carbon atoms (and bonded hydrogen atoms) that are labeled C2, C4, C5, Nτ and Nτ are of special interest in examining His-metal binding. Tautomer markers used to assign His-SeNP binding are listed in Table 2.

TABLE 2

Expected shifts of Histidine tautomers before and after metal binding.

| Tautomer Marker | Expected Shift (cm⁻¹) | Assignment* |
| --- | --- | --- |
| Nτ-H, Nπ | 1568-1573 | $C^4=C^5$ st |
|  | 1282-1287 | $N^\pi C^4$ st, $C^4 C^\beta$ st, $C^5 N^\tau$ st |
| Nτ-H, Nπ-M | 1573-1590 | $C^4=C^5$ st |
|  | 1272-1277 | $N^\pi C^4$ st, $C^4 C^\beta$ st, $C^5 N^\tau$ st |
| Nπ-H, Nτ | 1583-1588 | $C^4=C^5$ st + $N^\pi$H bending |
|  | 1260-1265 | $C^5$H def, $C^2$H def, $N^\pi C^2$ st |
| Nπ-H, Nτ-M | 1594-1606 | $C^4=C^5$ st $N^\pi$H bending |
|  | 1434-1440 | ring st |
| Nτ-H, Nπ-H | 1627-1634 | $C^4=C^5$ st |
|  | 1264-1269 | ring st |
| Nτ-M, Nπ-M | 1555-1567 | $C^4=C^5$ st |
|  | 1282-1292 | $C^2 N^\pi C^4$ st; $N^\pi C^4$ st, $C^4 C^\beta$ st, $C^5 N^\tau$ st |

*st = stretch; def = deformation.

The FIG. 6 peak spanning 1631-1636 cm⁻¹ correlates with the histidine C4-C5 stretch mode, consistent with a specific Nτ-H/Nπ-H protonation state ($HisH^{2+}$). This assignment is supported by the presence of the peak at 1268 cm⁻¹ (FIG. 10), which also corresponds to a $HisH^{2+}$ imidazolium ion. In the SeNP bound SeBP trace, the C4-C5 stretching mode downshifts to a broad peak centered at 1571 cm⁻¹. The features of this peak are shown in FIG. 6 with the vibration depicted. The region of the peak from 1565-1573 cm⁻¹ likely corresponds to a neutral imidazole form (HisH) that is unbound with the Nτ tautomer protonated and the Nπ unprotonated. The portion of the peak above 1573 cm⁻¹ likely corresponds with a metal bound His in the form Nτ-H/Nπ-M.

This assignment is supported by the shift in the band at 1268 cm⁻¹ (FIG. 6, panel B). Upon metal binding to SeNP with the tautomer form Nτ-H/Nπ-M, the band splits into a doublet with peaks at 1267 cm$^{-1}$ and 1271 cm$^{-1}$. The 1267 cm$^{-1}$ band is attributed to HisH in the form Nτ-H and unbound Nπ whereas the 1271 cm$^{-1}$ band correlates with a Nτ-H/Nπ-M form. The peak at 1556 cm$^{-1}$ is likely due to a metal bridging form of His (Nτ-M/Nπ-M) with the corresponding peak arising at 1292 cm$^{-1}$ (FIG. 6, panel B).

Overall, the Raman spectra of the peptide in the presence and absence of SeNPs support a specific interaction between SeBP and SeNPs. Here, SeNP binding is mediated primarily by previously described His-metal ligation interactions, and the aggregate of these interactions appears to drive a change in peptide backbone conformation that is consistent with a change from random coil to beta-sheet-like.

This work demonstrated the ability to alter enzymatic activity and product outcome of a SeNP producing enzyme, GRLMR. This is accomplished by fusion of a SeBP to the enzyme. The SeBP, selected from a phage display library against GRLMR produced SeNPs of ~8 nm, when studied exogenously did not show any propensity for size control or particularly strong SeNP binding. However, once fused to the C-terminal of GRLMR, improvements in resulting SeNP stability, size control, SeNP retention, and improved reduction rates of selenite were all observed. The outcome of this work proves exciting for the future identification of metal reducing enzymes which already can make inorganic nanostructures. In combination with substrate binding peptides that can also be expressed fused to the metal reducing enzyme, inorganic materials with defined characteristics can be produced in a completely green approach with everything but the inorganic salt being produced within a cell.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Materials and Methods

Materials

The Ph.D.™ Phage Display Kit, BSA, BspQI, T4 Ligase, Q5 High Fidelity polymerase, dNTPs, and BL21 (DE3) *E. coli* were purchased from New England Biolabs. Antibiotics were purchased from GoldBio. Na$_2$SeO$_3$ and HNaSeO$_3$ were purchased from Alfa Aesar. NADPH was purchased from BioVision and Coomassie Plus Bradford Reagent from Thermo Scientific. GeneJet Plasmid Miniprep Kit (Cat #K0503) and PCR Cleanup Kit (Cat #K0702) were purchased from ThermoFisher Scientific.

Protein Isolation and Characterization

Cultures of BL21 (DE3) cells (10 mL) containing the GRLMR-SeBP or GRLMR were started and grown O/N in a shaker at 37° C. and 225 RPM. The dense cultures were diluted into 1 L of LB Kan/Cam and allowed to grow until an OD$_{600}$ ~0.5-0.6. Induction was started using a 1 mM final concentration of IPTG and was supplemented with 1 μM of HNaSeO$_3$. Growth was O/N at 37° C. Cells were then spun down at 14000 RPM for 20 minutes and resuspended into B-PER and sonicated to lyse the cells. The insoluble cell debris was removed by centrifugation and the soluble cell lysate was collected for Ni-NTA purification. Nickel columns were prepared using Ni-NTA agarose beads. Beads were washed as follows: 3×3 column volumes of H2O, 3×3 column volumes of binding buffer (50 mM Tris-HCl (pH 8), 5 mM imidazole, 100 mM NaCl). The lysate was then run through the column 3× before 4 cycles of washing the column using washing buffer (50 mM Tris-HCl (pH 8), 20 mM imidazole, 300 mM NaCl). Finally, the column was incubated with column volume of elution buffer (50 mM Tris-HCl (pH 8), 300 mM imidazole, 50 mM NaCl) for at least 5 minutes before the elution buffer was collected. The isolated protein solution was dialyzed into PBS before the concentration was collected using UV-Vis and stored at −80° C. in aliquots for further study. A native PAGE gel was then run to ensure the positively charged SeBP was present on the isolated GRLMR.

Enzymatic SeNP Formation

100 μg of enzyme and aliquots of a 100 mM HNaSeO$_3$ solution were added to PBS, pH 7.4. The reaction was then started by the introduction of NADPH and allowed to react for several hours. After a several hours, the SeNPs were spun down and separated from the supernatant for further study.

Protein Bradford Assay

Stocks of enzyme in PBS, pH 7.4 at various concentrations were prepared of which 100 μL were diluted by 900 μL of Bradford reagent. Standard curves were collected for both the GRLMR and GRLMR-SeBP by monitoring the absorbance at 595 nm. Samples were then prepared for measurement in the same fashion by taking 100 μL of the target solution and diluting it up with 900 μL Bradford reagent. The concentration was then calculated by monitoring the absorbance at 595 nm.

PAGE Electrophoresis

Native gels were prepared as follows: 1.25 mL of 40% polyacrylamide, 1.25 mL of Tris buffer (pH 8.8), and 50 μL of a 10% ammonium persulfate (w/v) were diluted into 2.45 mL of milli-Q water with or without 50 μL of a 10% SDS solution for denaturing or native gels. Polymerization was initiated by adding 7 μL of TEMED before pouring the PAGE solution into a cast and allowing to solidify. PAGE gels were run in tris/glycine, pH 8.3 buffer with or without SDS at 150 V for 2.5 h at 4° C. For pH 6.6 PAGE gels, the gel buffer and running buffer was replaced with buffer containing 25 mM histidine and 30 mM MOPS giving a buffer of similar ionic strength and pH of 6.6. Gels were then submerged in Coomassie blue and microwaved for 30 sec and incubated for an addition 5 min at RT. Coomassie stain was then replaced by milliQ water and microwaved for 5 min, then washed again in the same way before imaging. Native gels would also be run and later soaked in 5 mM HNaSeO$_3$ and 1 mM NADPH inside of a plastic bag under nitrogen. These gels would result in red bands of reduced selenium that could then be visualized the next day.

Dynamic Light Scattering

Reactions for DLS monitoring were prepared in disposable plastic cuvettes as described above. SeNP formation was monitored using a refractive index of 2.6 and an absorbance of 0.5 for α-Se and a refractive index and viscosity of PBS of 1.332 and 0.8898 cP, respectively. Reactions ran for at least 4 hours at RT.

$K_M$ and $k_{cat}$ Studies

Initial velocities ($V_0$) of the GRLMR-SeBP were performed in various concentrations of HNaSeO$_3$ or GSSG while monitoring 340 nm correlating to NADPH absorbance. The reactions were run in PBS, pH 7.4 and with 13 μg of enzyme with substrate SeO$_3$$^{2-}$ (1.5 μg of enzyme with substrate GSSG) and 200 μM of NADPH with 0.05 mM-2 mM of substrate. Enzymatic $V_0$s were plotted against substrate concentration in OriginPro from which $K_M$ and $k_{cat}$ could then be calculated.

Synthesis of SeBP Capped Selenium Nanoparticles (SeBP/SeNPs)

Peptide-capped SeNPs were synthesized based on established methods. For the SeNPs, 50-100 μL of acidic 10 mM $SeO_3^{2-}$ and 0.5-1.0 mL of 10 mM $NaBH_4$ (aq) were added to a 15 ml conical tube and diluted to a final volume of 1.5-3.0 mL with milliQ water. The solution was mixed and placed on a rocker for 90-300 seconds, after which 50-100 μL of 10 mM of the SeBP was added and thoroughly mixed into the solution and placed back on the rocker. Within 10 minutes the tube was placed in an ice bag and allowed to conjugate for 4 hours on the rocker. After this, the solution was dialyzed using a 3,500 MWCO cassette on ice in 2.0 L milliQ water for at least 2 hours. The resulting mixture was lyophilized and stored in a refrigerator until future analysis. The sample was diluted into 50 μL PBS, pH 7.4.

Raman Spectroscopy

Raman spectra were collected using an inverted Raman microscope with an Olympus IX73 frame and objectives with a Horiba iHR 550 Spectrometer with a neural synapse thermoelectrically cooled charge-coupled device (CCD) detector attached to a Horiba ONDAX T-Hz Raman 532 nm laser provided by Justin Sambur. This setup was accompanied with a LabSpec software package. The specimen was prepared by drop-casting 3-7 μL of sample onto a glass cover slip and allowed to dry in air at room temperature. Double-sided tape to seal the sample and to adhere the coverslip to a glass slide was used. Spectra were collected using an incident laser power of 83 mW. A 60× water objective with a 1200 blazes/mm grating, which has a resolution of approximately 2 $cm^{-1}$ per pixel was used. The laser was manually focused on the sample using the optical setup. If signal was insufficient, the laser was refocused until signal was obtained. The software's denoiser program was used, which is a smoothing algorithm, to obtain a smoother curve. Backscatter collection ranged from 30-300 seconds per acquisition, and a total of 1-15 spectra were accumulated and averaged, depending on the level of noise. Any spikes caused by cosmic rays were removed using the software's spike removal function.

Figure 7:
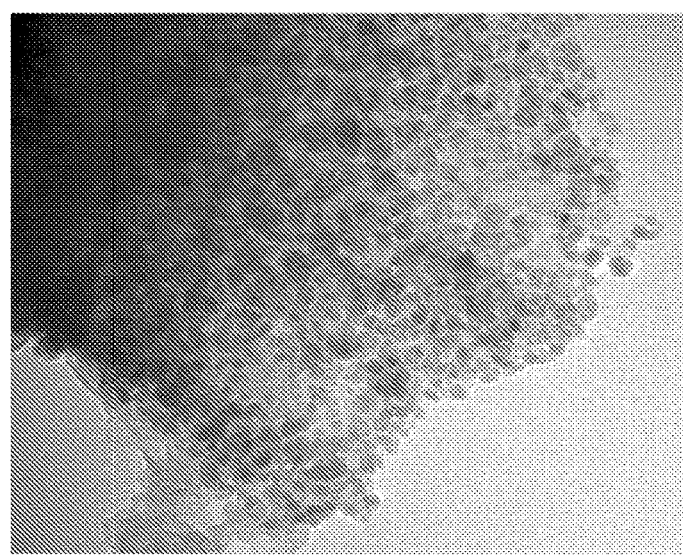
FIG. 7. GRLMR produced SeNPs for peptide selection. Scale bar=50 nm.

Phage Binding Assay:

Initial preparation of the plate for SeNP binding assays were prepared as follows: in a 96-well polystyrene plate a mixture of GRLMR, selenite and NADPH at concentrations previously found to produce ~5 nm SeNPs was added to 3×23 wells in 100 μL aliquots (FIG. 7). The wells then incubated overnight at RT with agitation and then spun for 2 hr at 4000 RPM and 4° C. Supernatant was then dumped and a 100 μL of a solution of filter sterilized 5 mg/mL BSA and 0.1 M $NaHCO_3$, pH 8.6 was then added to each well and allowed to incubate for at least 1 hour under agitation at 4° C. This solution was then dumped, and the wells were then washed 6 times with TBS supplemented with 0.1% [v/v] Tween-20. 100 μL of a phage solution diluted to $10^{11}$ pfu in TBS supplemented with 0.1% [v/v] Tween-20 was added to the first 23 wells. Phage was permitted to bind for 60 minutes after which time the excess solution was dumped from the wells. Wells were then rapidly washed with 10 times with a TBS buffer supplemented with 0.25% [v/v] Tween-20 to remove weak binding phage. These steps were repeated 2 times for a total of 3 rounds of selection with more stringent binding and washing steps to ensure stronger binders would be collected. In round 2 the wash step was performed using TBS supplemented with 0.5% [v/v] Tween-20. In round 3 the binding step was reduced to 10 minutes and washing was done using TBS supplemented with 0.5% [v/v] Tween-20. Bound phage was eluted after each wash step using 100 μL of a 0.2 M glycine-HCl, pH 2.2, BSA 1 mg/mL solution in each well for 15 minutes. This solution was then immediately neutralized using 1 M Tris-HCl, pH 9.1. Negative binding assays were run similarly with wells being coated with either BSA, unreacted GRLMR, or SiNPs in a 0.1 M $NaHCO_3$, pH 8.6.

Phage Titers:

Phage titers were performed using *E. coli* ER2738 from the NEB Ph.D.™ Phage Display Kit. Initially, ER2738 cells were plated on a clean LB Agar plate supplemented with tetracycline and grown overnight. A small volume of LB with tetracycline was inoculated with a colony of ER2738 and grown overnight at 37° C. and 225 RPM. A volume of LB required for the titers was then inoculated the next day and grown to an $OD_{600}$ ~0.4. A phage solution was then diluted in the ranges of $10^1$-$10^8$. In a 96-well plate, 180 μL of the cells was added to several wells that corresponds to the number of dilutions to be titered. 20 μL of the diluted phage solutions were added to the corresponding wells and infection was allowed for 30 minutes. After infection, 3×10 μL of infected cells were deposited on a LB plate containing Xgal and IPTG in a β-galactosidase based identification of infected cells. The plate was then grown overnight at 37° C. and the next day blue spots, correlating to the number of infected colonies were counted. The number of infected colonies could then be multiplied by the dilution factor to give an estimate on the concentration of phage in the phage solutions.

SeBP Identification:

Isolation of SeNP binding peptides was accomplished using a New England Biolabs PhD phage display library (Catalog #E8110S). This kit contains a library of 109 unique dodecapeptides expressed on the pIII protein of M13 bacteriophage. Selection was against GRLMR produced SeNPs of 8.4±2.7 nm in diameter, confirmed by TEM (FIG. 7). These SeNPs were adhered nonspecifically to a polystyrene 96-well plate. Following standard blocking and washing steps, the immobilized SeNPs were exposed to the phage library. To isolate phage that display peptide sequences that bind to SeNPs, the phage solution was first diluted to 109 plaque forming units (pfu) for all binding steps. Phage binding to SeNPs proceeded for 1 hour in selection rounds 1 and 2 but was reduced to 10 minutes in round 3. After the allotted binding time, supernatant was removed, and the SeNP coated 96-well plate washed to remove any remaining unbound phage. In selection rounds 2 and 3, detergent concentrations in the wash step were increased, to remove less favorably bound peptides. After each selection round, bound phage were acid-eluted with a Glycine-HCl (pH 2.2) based elution buffer for 20 minutes.

DNA sequencing of the $3^{rd}$ round eluted phage revealed an evolved library dominated by two sequences, LTPHKHHKHLHA (SeBP; SEQ ID NO: 1) and GPHHMHHHRTHH (SeBP2; SEQ ID NO: 2). Seven other sequences were also found. FIG. 8 illustrates relative residue identity frequency at each position in the peptide.

To control for the possibility of non-specific binding to either polystyrene or to non-selenium inorganic particles, negative selections were attempted using 20 nm Silica nanoparticles, GRLMR, and a polystyrene surface. Negative binding assays were performed in triplicate and eluted phage were immediately titered against *E. coli* in a beta-galactosidase based assay. The peptides chosen for the negative binding assays are highlighted in yellow and were of interest because of their sequencing frequency or picked randomly for comparison. Table 3 shows the phage titer resulting eluted from each negative binding target. For reference, each titer began with an initial phage titer of $10^{10}$ pfu.

TABLE 3

Sequences identified after the selection against GRLMR produced SeNPs. Each sequence is described by population distribution, the number of positive and negative residues, and the results of the negative selection screens against BSA, unreacted GRLMR, and SiNP in pfu. Wild Type indicates the presence of no inserted sequence.

| | Pep. Seq. Wild Type | Frequency N/A | pI N/A | Polystyrene $3.9 \times 10^4$ | GRLMR $1.5 \times 10^5$ | SINP $1.8 \times 10^4$ |
|---|---|---|---|---|---|---|
| SeBP | LTPHKHHKHLHA (SEQ ID NO: 1) | 19/33 | 9.37 | $3.7 \times 10^4$ | $2.6 \times 10^5$ | $3.0 \times 10^5$ |
| SeBP2 | GPHHMHHHRTHH (SEQ ID NO: 2) | 7/33 | 10.47 | $1.1 \times 10^9$ | $2.1 \times 10^9$ | $7.9 \times 10^9$ |
| SeBP3 | WPRHHWHTNYMR (SEQ ID NO: 3) | 1/33 | 11.15 | $2.3 \times 10^8$ | $3.9 \times 10^8$ | $1.3 \times 10^8$ |
| SeBP4 | GWHSPHAHWRVK (SEQ ID NO: 4) | 1/33 | 10.61 | $4.3 \times 10^4$ | $3.3 \times 10^5$ | $3.7 \times 10^5$ |
| SeBP5 | THYNPLRINPIT (SEQ ID NO: 5) | 1/33 | 9.95 | $9.8 \times 10^3$ | $6.8 \times 10^5$ | $1.8 \times 10^4$ |
| SeBP6 | KVHIMHFHHHSL (SEQ ID NO: 6) | 1/33 | 9.08 | N/A | N/A | N/A |
| SeBP7 | HSWSTIKRIETM (SEQ ID NO: 7) | 1/33 | 9.07 | N/A | N/A | N/A |
| SeBP8 | WPHLQHHKATSR (SEQ ID NO: 8) | 1/33 | 10.61 | N/A | N/A | N/A |
| SeBP9 | HDRMTKSSFSPP (SEQ ID NO: 9) | 1/33 | 9.07 | N/A | N/A | N/A |

Based on this titer, SeBP, SeBP4, and SeBP5 show comparable binding to all of the negative targets as phage that display no peptide (wild type, wt). In comparison SeBP2 and SeBP3 show notable binding to polystyrene, GRLMR, and SiNPs, indicating that these are relatively nonspecific binders. Therefore, SeBP2 and SeBP3 was eliminated from further investigation. Since SeBP1 represented most of the evolved pool and didn't incorporate substantial nonspecific binding, this peptide was further investigated.

Insertion of SeBP into the GRLMR Gene:

Primers were designed for outward PCR one of which containing the sequence encoding the identified SeBP1 and BspQI restriction sites to allow for eventual restriction digestion and ligation of the linear PCR product. Outward PCR was run with a 100 nM final concentration of each primer, 100 µg of template, 200 µM dNTPs, 10 µL of Q5 buffer, 10 µL of GC Enhancer, 1U of NEB's Q5 High-Fidelity Polymerase and brought up to 50 µL with milli-Q water. Denaturing of the template at 98° C. for 1 min followed by 37 cycles of a 10 sec denaturing at 98° C., 65° C. for 20 sec, and extension at 72° C. for 2 min and 45 sec. A final 2 min extension at 72° C. to finish any incomplete extensions. Remaining templates were digested by DpnI for 1 h then remaining PCR product was cleaned using the Thermo Gene-jet PCR purification kit and eluted with 50 µL of milli-Q water for future digestion and ligation. 1 µg of PCR product was then digested at 50° C. for at least 1 h using 10 U of BspQI, 5 µL NEB Buffer 3.1, and a final volume of 50 µL using milli-Q water. The restriction digestion was again cleaned using the Thermo purification kit and eluted using 40 µL of milli-Q water. Circularization was performed on 50 ng of digested product with 200 U of T4 ligase, 5 µL of T4 buffer, 1 µL supplemental ATP diluted to a final volume of 50 µL with milli-Q water at 22.5° C. for 45 min before denaturing of the ligase at 65° C. for 10 min.

Cell Heat Shock Transformation:

65 µL of chemically competent cells was mixed with 6.5 µL of the ligation mixture and allowed to incubate on ice for at least 5 min. The tube was then put into a 42° C. water bath for ~45 sec before being placed back on ice for another 2 min. The transformed cells were then transferred to pre-warmed LB and allowed to recover at 37° C. for at least an hour before plating on an LB agar plate containing the corresponding antibiotic for plasmid selection. The plate was incubated at 37° C. until colonies were visible for picking and sequencing. Sequenced confirmed colonies were then used to express and isolate the GRLMR-SeBP. GRLMR-SeBP was run on Native-PAGE and eiter soaked in Coomassie stain or in $SeO_3^{2-}$ and NADPH to check for enzyme activity (Figure. 9)

pH 6.6 Native PAGE Gel:

Native PAGE gels were prepared and run following the preparation established previous previously (Anal. Biochem. 1982, 126 (1), 94). Buffer for the PAGE gel was composed of a final concentration of 25 mM Histidine and 30 mM MOPS instead of the common Tris/Glycine buffer. Gels were prepared and run at 4° C. for >4 hours. Gels were then stained using either Coomassie stain or $SeO_3^{2-}$/NADPH solution. Results indicate a pI for GRLMR-SeBP as being close to pH 6.6 as the migration was minimal.

Example 2. Model for Cloneable Nanoparticles

Figure 12A:
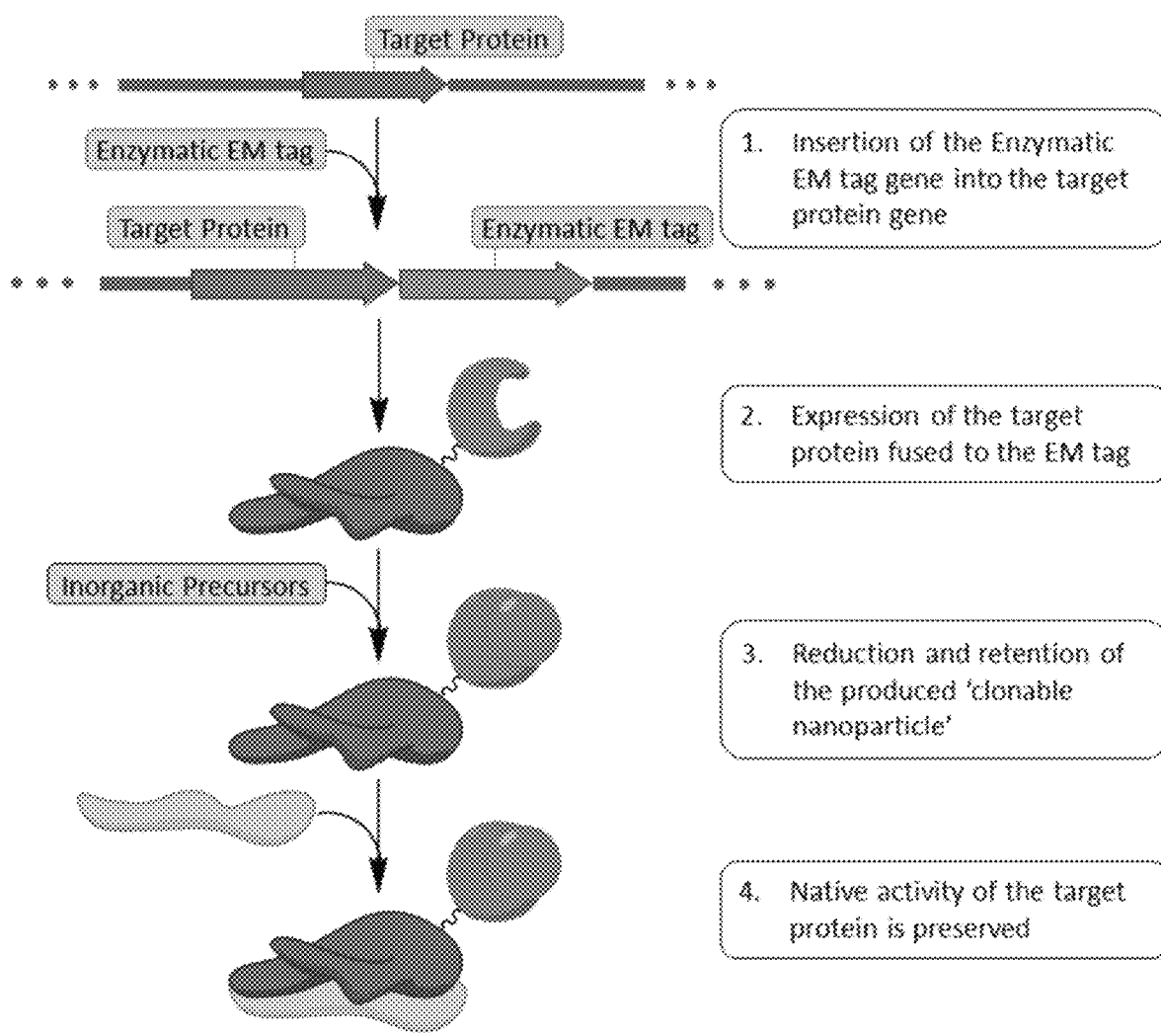
FIG. 12A-B. (A) Flowchart showing a fusion of GRLMR tag to a targeted protein is first prepared on a plasmid. (B) Nanoparticles are formed and can be imaged after the fusion protein is expressed in cells containing the plasmid.
Figure 12B:
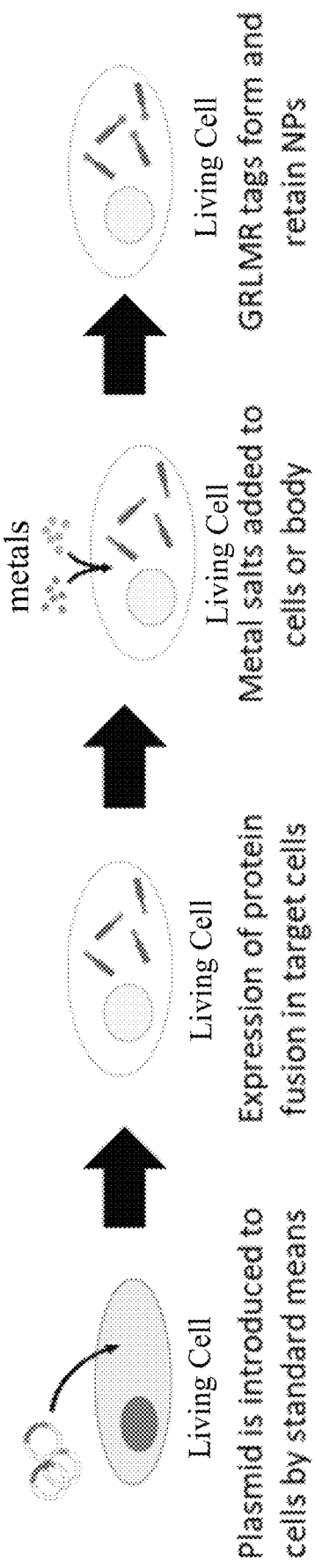
Figure 13:
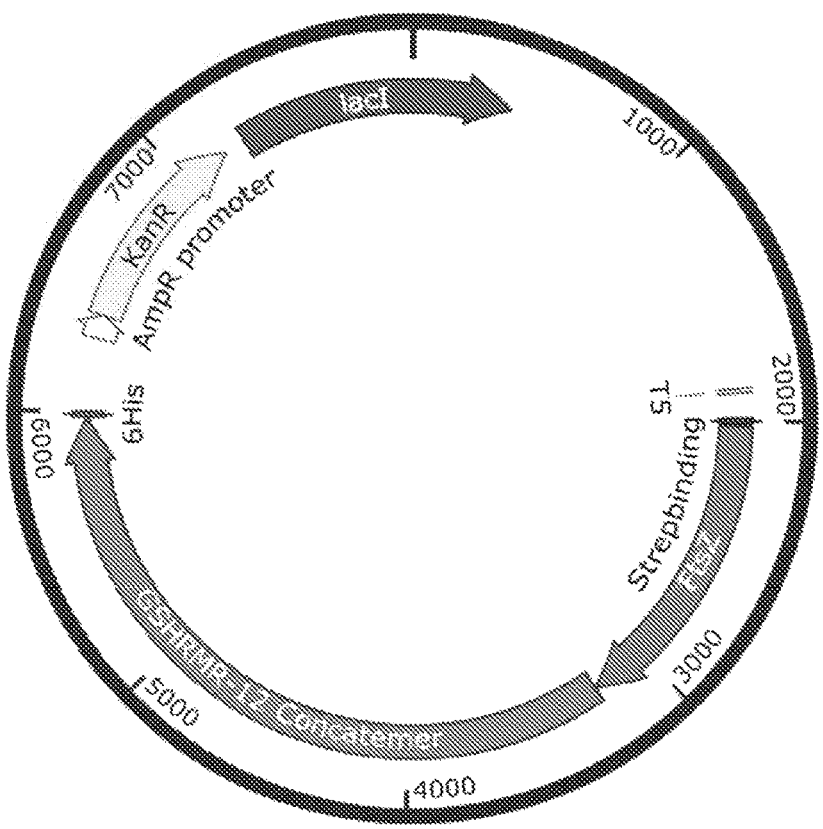
FIG. 13. Construction and in vivo observation of the EM tag. Plasmid used containing the GSHRMR-12 concatemer fused to the *E. coli* tubulin-analogue protein FtsZ.
Figure 14:
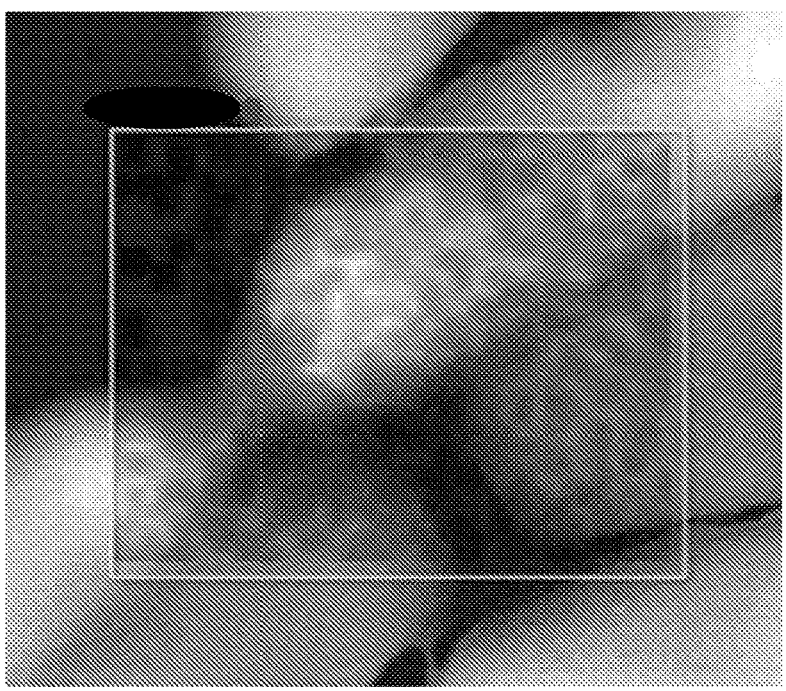
FIG. 14. TEM image and overlaying EDS maps of *E. coli* grown with a short induction with IPTG of the GSHRMR-12 concatemer tag and a short incubation time in selenite. Selenium (dark speckles) localized at the pinch point of the cells as the division progresses. Image indicates the presence of active EM tagged FtsZ with SeNPs at the Z-ring to cause the separation of the two cells.

The flowchart in FIG. 12 shows how a metal/metalloid reducing enzymatic gene is cloned into a gene of interest (FIG. 13) and when expressed produces a fusion protein of the target protein and the redox active tag. Incubation with the metal salt precursors leads to the reduction or the precursors and subsequent nucleation and growth of an inorganic NP. In order to increase the baseline retention of NPs by the enzyme, a peptide selected specifically for SeNPs was identified and fused to the enzymatic tag. A concatemer was produced of the GRLMR and fused to the *E. coli* protein FtsZ, a tubulin analogue to explore the activity of both the enzymatic tag and the FtsZ target protein. Transmission electron microscopy (TEM) images of FtsZ undergoing cell division is shown in FIG. 14.

A glutathione reductase-like metalloid reductase, GRLMR isolated from *Pseudomonas moraviensis* stanleyea acts as the cNP enzyme for its Se-reductase activity. An identified Se-binding peptide (SeBP) would also be fused to GRLMR conferring better activity, size control, and affinity to the Se-nanoparticle (SeNP) product. FtsZ, a tubulin homologue present in bacteria would act as the model system. FtsZ is a polymerizing protein responsible for forming the Z-ring in dividing bacterial cells. The Z-ring is responsible for pinching off a bacterium into two daughter cells. FtsZ is of interest to this study as it has been explored extensively as a possible target for anti-bacterial medicines. FtsZ structures have been observed in vitro and in vivo utilizing both EM and fluorescence microscopy. Overproduction of FtsZ, or the production of FtsZ in foreign hosts, often leads to longitudinal filaments formed in the cytoplasm. Structures observed by FtsZ tagged with GFP on the N- and C-term extended from formation of a proper Z-ring, periodic aggregates, and coils. In vitro, FtsZ can form filaments, clumped filaments, coils, and rings depending on the polymerization environment, i.e. GTP/GDP, divalent cations, crowding molecules, interacting proteins, and pH. Capable of being isolated in large quantities and maintaining function in a wide range of environments makes FtsZ an excellent model system for purposes of cNP optimization.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A fusion protein comprising a target protein and a redox-active tag,
   wherein the redox-active tag comprises:
   a) a metalloid reductase that reduces a metal salt to a metal nanoparticle; and
   b) a metal nanoparticle binding peptide comprising the amino acid sequence of LTPHKHHKHIHA (SEQ ID NO: 1) wherein the metal nanoparticle binding peptide binds the metal nanoparticle; and
   wherein the metal nanoparticle binding peptide is fused directly to the metalloid reductase.

2. A plasmid comprising a nucleotide sequence encoding the fusion protein of claim 1.

3. A method for detecting cloned nanoparticles in cells comprising:
   a) providing cells comprising the plasmid of claim 2 and expressing the fusion protein in the cells to form tagged cells;
   b) incubating the tagged cells with a metal salt to form cloned nanoparticles via enzymatic reduction of the metal salt by the metalloid reductase to form a cloned nanoparticle and retention of the cloned nanoparticle by the metal nanoparticle binding peptide; and
   c) detecting the cloned nanoparticles at the target protein in the cells.

4. The method of claim 3 wherein the metalloid reductase is glutathione reductase-like metalloid reductase (GSHRMR).

5. The method of claim 4 wherein the GSHRMR reduces a salt of selenium to selenium (0) metal.

6. The method of claim 5 wherein the metal nanoparticle binding peptide binds and retains the selenium (0) via histidine moieties.

7. The method of claim 3 wherein the cloned nanoparticles have a diameter of 1 nm to 250 nm.

8. The method of claim 3 wherein a size distribution of the cloned nanoparticles is characterized by a root mean square (rms) deviation in diameter of less than 25%.

9. The method of claim 3 wherein detecting the cloned nanoparticles at the target protein in the cells is performed by scanning electron microscopy (SEM) or optical microscopy.

10. The method of claim 3 wherein the target protein is a protein from a bacterium or a virus.

11. The fusion protein of claim 1, wherein the metal nanoparticle binding peptide consists of the amino acid sequence of LTPHKHHKHLHA (SEQ ID NO: 1).

12. The fusion protein of claim 1, wherein the metal nanoparticle binding peptide is a selenium nanoparticle binding peptide.

13. The fusion protein of claim 1, wherein the metal nanoparticle binding peptide is capable of binding a selenium (0) nanoparticle.

14. The fusion protein of claim 1, wherein the metalloid reductase is GSHRMR.

15. The fusion protein of claim 1, wherein the metalloid reductase is capable of reducing a selenium oxyanion to a selenium nanoparticle.

16. The fusion protein of claim 1, wherein the metal salt is a selenium salt.

17. The fusion protein of claim 1, wherein the metalloid reductase is GSHRMR and the metal nanoparticle binding peptide is a selenium nanoparticle binding peptide.

18. The fusion protein of claim 1, wherein the metalloid reductase is GSHRMR, the metal nanoparticle binding peptide is a selenium nanoparticle binding peptide, and the metal salt is a selenium salt.

19. The fusion protein of claim 1, wherein the metal nanoparticle is a selenium nanoparticle.

20. The fusion protein of claim 1, wherein the metal nanoparticle has a size of 5.0±1.0 nm.

21. The fusion protein of claim 1, wherein the metal nanoparticle is a chalcogen nanoparticle.

* * * * *

SEQUENCE LISTING

```
<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Thr Pro His Lys His His Lys His Leu His Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Pro His His Met His His His Arg Thr His His
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Pro Arg His His Trp His Thr Asn Tyr Met Arg
1               5                   10
```

```
<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Trp His Ser Pro His Ala His Trp Arg Val Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr His Tyr Asn Pro Leu Arg Ile Asn Pro Ile Thr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Val His Ile Met His Phe His His His Ser Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ser Trp Ser Thr Ile Lys Arg Ile Glu Thr Met
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Pro His Leu Gln His His Lys Ala Thr Ser Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
His Asp Arg Met Thr Lys Ser Ser Phe Ser Pro Pro
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5
```